United States Patent
Ohta et al.

(10) Patent No.: US 8,796,654 B2
(45) Date of Patent: Aug. 5, 2014

(54) SCAN DEVICE FOR MICROSCOPE MEASUREMENT INSTRUMENT

(75) Inventors: Masahiro Ohta, Kyoto (JP); Noriaki Oyabu, Kyoto (JP); Kenjiro Kimura, Kobe (JP); Shinichiro Ido, Kyoto (JP); Kei Kobayashi, Kyoto (JP); Hirofumi Yamada, Kyoto (JP); Kazumi Matsushige, Kyoto (JP)

(73) Assignee: Shimadzu Coporation, Kyoto-Shi (JP)

( * ) Notice: Subject to any disclaimer, the term of this patent is extended or adjusted under 35 U.S.C. 154(b) by 682 days.

(21) Appl. No.: 13/056,293

(22) PCT Filed: Jul. 31, 2008

(86) PCT No.: PCT/JP2008/002057
§ 371 (c)(1),
(2), (4) Date: May 9, 2011

(87) PCT Pub. No.: WO2010/013288
PCT Pub. Date: Feb. 4, 2010

(65) Prior Publication Data
US 2011/0261352 A1  Oct. 27, 2011

(51) Int. Cl.
*G01N 21/86* (2006.01)
*G01V 8/00* (2006.01)
*G01N 35/10* (2006.01)
*G01Q 10/06* (2010.01)
*H01J 37/20* (2006.01)
*H01J 37/26* (2006.01)
*H01J 37/28* (2006.01)
*B82Y 35/00* (2011.01)

(52) U.S. Cl.
CPC ............. *G01N 35/1011* (2013.01); *B82Y 35/00* (2013.01); *G01Q 10/065* (2013.01); *H01J 37/20* (2013.01); *H01J 37/265* (2013.01); *H01J 37/28* (2013.01); *H01J 2237/20228* (2013.01)
USPC ....................... 250/559.06; 250/206; 250/234

(58) Field of Classification Search
CPC ..... H01J 37/28; H01J 37/268; H01J 2237/28; H01J 37/292; H01J 37/2955

USPC ......... 250/310, 234, 306, 206, 208.2, 559.06, 250/227.26; 369/126; 73/105; 356/72, 319
See application file for complete search history.

(56) References Cited

U.S. PATENT DOCUMENTS

| | | | |
|---|---|---|---|
| 2003/0112475 A1* | 6/2003 | Shoda et al. | 358/474 |
| 2005/0199046 A1* | 9/2005 | Shikakura et al. | 73/105 |
| 2006/0067575 A1* | 3/2006 | Yamada | 382/176 |
| 2006/0113472 A1* | 6/2006 | Shigeno et al. | 250/310 |

FOREIGN PATENT DOCUMENTS

| | | |
|---|---|---|
| JP | 02-265155 | 10/1990 |
| JP | 05-164511 | 6/1993 |
| JP | 06-137811 | 5/1994 |
| JP | 07-159419 | 6/1995 |
| JP | 2000-329680 | 11/2000 |

OTHER PUBLICATIONS

International Preliminary Report on Patentability for the counterpart International application No. PCT/JP2008/002057.

* cited by examiner

Primary Examiner — Francis M Legasse, Jr.
(74) Attorney, Agent, or Firm — Bingham McCutchen LLP

(57) ABSTRACT

A probe needle is successively moved to a plurality of measurement points set in a measurement region on a sample so as to measure a z-displacement amount. An excitation control unit feedback-controls a piezoelectric element so that a vibration amplitude of a cantilever is constant in accordance with the detection output by a displacement detection unit. Moreover, a vertical displacement control unit feedback-controls a vertical position scan unit so as to obtain a constant distance between the probe needle and the sample according to a frequency shift by a frequency detection unit. When changes of outputs of two feedback loops at a certain measurement point are both within a predetermined range, a main control unit issues an instruction to a horizontal position control unit to rapidly move to the next measurement point. As a result, it is possible to adaptively decide such a measurement time that both of the two feedback controls at respective measurement points are established. This eliminates an unnecessary measurement time, which in turn reduces the time required for creating one convex/concave image as compared to the conventional technique and improves the throughput.

11 Claims, 21 Drawing Sheets

Conventional device

Conventional device

Device according to the present invention

Device according to the present invention

Device according to the present invention

Device according to the present invention

SCAN DEVICE FOR MICROSCOPE MEASUREMENT INSTRUMENT

CROSS-REFERENCE TO THE RELATED APPLICATIONS

This application is a national stage of international application No. PCT/R2008/002057, filed on Jul. 31, 2008, the entire contents of which are incorporated herein by reference.

TECHNICAL FIELD

The present invention relates to a scan device used in a measurement instrument for scanning a plurality of measurement points wherein physical quantities of a sample are measured/detected at each measurement point by sequentially scanning a plurality of measurement points that are defined on a sample, or to a scan device used in a measurement instrument that measures/detects a physical quantity of a sample by sequentially scanning a plurality of measurement points that are defined in terms of a physical quantity such as frequency, wavelength or mass-to-charge ratio m/z.

BACKGROUND ART

Many measurement instruments work by sequentially scanning measurement points that are defined on the object to be measured and performing the measurements at each measurement point, or by sequentially scanning (changing) a physical parameter while performing the measurements. Examples of measurement instruments that perform measurements while scanning the measurement points of a sample being measured include atomic force microscopes, scanning electron microscopes, imaging mass spectrometers and the like. Examples of measurement instruments that scan frequency as a physical parameter while making measurements include spectrum analyzers, network analyzers and the like. Examples of measurement instruments that scan across a wavelength of light as a physical parameter include ultraviolet-visible spectrophotometers, infrared spectrophotometers, fluorophotometers and the like. An example of a measurement instrument that scan m/z as a physical parameter while making measurements is a mass spectrometer.

The description hereinbelow focuses primarily on surface analysis instruments such as atomic force microscopes and scanning electron microscopes which are used for the measurement of surface shapes of samples. With such analytic instruments, a predetermined area on a sample is two-dimensionally scanned, and measurements of a very small area on the sample are repeatedly taken to determine, for example, the distribution of certain measurement results in a predetermined area. For example, with atomic force microscopy (AFM), images representing concavities and convexities of the surface of a sample are obtained by one-dimensionally or two-dimensionally scanning the surface of the sample while feeding back and controlling the distance between a sharply pointed probe needle and a sample's surface so that a signal that depends on the distance is kept constant.

Frequency modulation atomic force microscopy (FM-AFM) is a type of atomic force microscopy where a cantilever—which holds a probe needle that approaches the surface of a sample to an atomic level of distance—is made to vibrate at its mechanical resonant frequency so that changes in resonant frequency (frequency shift) caused by interaction between the probe needle and the sample surface can be detected. Since the frequency shift depends on the distance between the probe needle and the sample surface, the sample's surface is two-dimensionally scanned (e.g., raster scanned) in a plane orthogonal to a direction normal to the sample's surface while keeping the frequency shift constant. In this way, concave/convex images of the sample's surface are obtained. Feedback control is performed in this case to keep the distance between the sample and the probe needle constant. At the same time, feedback control is performed to keep the amplitude of the vibration of the probe needle constant.

Generally speaking, with the aforesaid atomic force microscopy, the measurement time (dwell time) spent at each measurement point of the sample is predetermined, and the time required for moving from one measurement point to the next measurement point is sufficiently shorter than the measurement time at each measurement point so that the overall time spent for the measurements, i.e., the time required for obtaining the convex/concave images of the sample's surface, depends on the number of measurement points. With a feedback control such as the afore-described where the separation distance between the probe needle and the sample is kept constant, some time is required after moving to a measurement point for the separation distance to converge to a certain value as determined by factors such as the response characteristics of the feedback control loop. This means that if the measurement time that is defined for each measurement point is too short, measurement values are acquired before the separation distance had converged to a certain value, and the resulting surface shape images that are obtained become inaccurate. At worst, the probe needle may contact the sample surface, damaging either or both and making continued measurements impossible. To avoid these problems, an amount of time has to be calculated that will allow feedback control on the separation distance to sufficiently stabilize even assuming maximum variations in the concavities and convexities and to set a measurement time for each measurement point that is longer than the calculated stabilization time.

However, if that is done, the measurement time at each of the measurement points generally becomes long, and the time required for performing the measurements at all measurement points becomes very long. The result is poor measurement efficiency and reduced throughput. One application of FM-AFM is Kelvin force microscopy (KFM) which performs measurements while compensating for potential differences. With KFM, in addition to the two afore-described feedback control loops found in ordinary FM-AFM, a feedback control loop is provided to compensate for the potential differences that occur at the probe needle. This third feedback control loop includes a lock-in amplifier for measuring the potential difference, and the time required for its stabilization is longer than that of the other feedback control loops. Because of this, the overall measurement time becomes unavoidably long even when the sample being measured has a surface that is relatively flat and changes in potential difference occur only locally.

As described in Patent Literature 1, a known procedure with previous scanning tunneling microscopes is to adjust the measurement time depending on the concavity and convexity of the sample's surface when performing feedback control to keep a constant separation distance between the probe needle and the sample while scanning the measurement points. However, because of the use of a plurality of feedback control loops in FM-AFM, KFM and the like for controlling factors that cause variations during a scan, a problem with the afore-described previous art is the inability to perform a suitable scan control.

Another problem with the previous art is that control that uses the afore-described conventional art cannot be used with instruments such as scanning electron microscope where scanning is usually performed without using a feedback control.

Patent Literature 1: JP 05-164511 A

DISCLOSURE OF THE INVENTION

Problems To Be Solved By the Invention

The present invention has been made for solving the afore-described problems. It is the object of the present invention to provide a scan device for use with both measurement instruments that perform scanning accompanied by a plurality of feedback controls and those that perform scanning without using a feedback control so that the measurement time is shortened and the throughput increased without sacrificing measurement accuracy.

Means For Solving the Problems

To solve the afore-described problems, the first invention is a scan device for use with a measurement instrument which performs measurements by sequentially scanning each of a plurality of measurement points that are defined on a sample or a measurement instrument which performs measurements by sequentially scanning each of a plurality of measurement points defined in terms of a physical measurement condition, the scanning device including:

a) n (where n is any integer equal to or greater than 2) conditional decision means for judging whether or not a condition defined in advance has been satisfied by each measurement point; and b) a scan control means which, if a decision is made by the n conditional decision means that all conditions have been satisfied by each measurement point, spatially moves the sample or the measurement system or changes the physical condition so as to move to the next measurement point.

With the scan device according to the first invention, if all n conditions are met before the passage of a predetermined time after moving from one measurement point to the next measurement point, the scan promptly movers to the next measurement point. Hence, the measurement time that is spent at each measurement point is determined by the time required for all conditions to be satisfied at the particular measurement point. In general, this measurement time is not the same for all measurement points, and the measurement time may be long or short. If the same measurement time is used for all measurement points as was clone previously, the measurement time has to be set to accommodate the measurement point with the worst conditions. This means that for many measurement points, the measurement time becomes unnecessarily long. In contrast to this, with the scan device according to the first invention, because the measurement time is adaptively determined for each measurement point, unnecessarily long measurement time is not used. The result is a great reduction in the total time required for performing measurements at all measurement points as compared to the previous ways.

Furthermore, with the scan device according to the first invention, the scan does not move to the next measurement point merely because some of the n conditions have been satisfied. Because the movement to the next measurement point occurs only after the conditions necessary for obtaining an accurate measurement at a particular measurement point are met and an accurate measurement value is obtained, even though the overall measurement time is reduced, the accuracy of the measurements is not sacrificed, and measurements of a high accuracy are guaranteed.

In moving from one measurement point to the next measurement point, one mode of the scan device according to the first invention uses at least two feedback controls by changing a physical condition or by spatially moving the sample or the measurement system. The n conditional decision means can be configured to judge whether or not the output of the feedback control loops used for the feedback control is either constant or the variation in the output falls within an acceptable range.

Another mode of the scan device according to the first invention uses at least two feedback controls in moving from one measurement point to the next measurement point by changing a physical condition or by spatially moving the sample or the measurement system. The n conditional decision means can be configured to judge whether or not the difference between a target value and an input value to the feedback control loops used for the feedback control is either zero or falls within an acceptable range.

A typical example of a scan device according to these modes is a scan device that is used with a frequency modulation atomic force microscope (FM-AFM) where scanning is performed while maintaining a relative distance between the sample and the probe needle. In this case, the feedback controls consist of controlling the separation distance between the probe needle and the sample and controlling the vibration amplitude of the probe needle (cantilever).

Another example of a scan device according to the above modes is a scan device that is used with a Kelvin force microscope where scanning is performed while keeping a relative distance between the sample and the probe needle. In this case, in addition to the afore-described control on the separation distance between the probe needle and the sample and the control on the vibration amplitude of the probe needle, a feedback control loop is provided for compensating for the potential difference across the probe needle and the sample. In other words, three feedback control loops are provided. This means that, with this scan device, the movement from one measurement point to the next measurement point happens when all three conditions are satisfied.

Furthermore, if the n conditional decision means are used to judge whether or not the change or difference in output falls within an acceptable range, it is acceptable for a means to be provided that allows a user to specify the acceptable range. By configuring in this way, the user is free to set an acceptable range that fits the purpose of the measurements or the type of sample being measured, For example, if a greater importance is given to throughput over measurement accuracy, the acceptable range can be set to be relatively wide whereas if a greater importance is given to measurement accuracy over throughput, the acceptable range can be set to be relatively narrow.

Furthermore, if the a conditional decision means are used to judge whether or not the change or the difference in output falls within an acceptable range, it is acceptable to provide a range determination means for automatically calculating the acceptable range based on output values from a feedback control loop at two or more different measurement points already scanned, For example, the range determination means can decide on an acceptable range to be proportional to the inverse of the mean or the difference (change) in the outputs from the feedback control loop at two or more different measurement points where a scan has already been performed. By so doing, the acceptable range can be made narrow where concavities and convexities of the sample surface are large so that measurements of a high precision are performed, and the acceptable range can be made automatically made broad in areas where the sample surface is flat so as to increase the resistance against noise. Furthermore, it is possible to allow a user to set a lower limit and an upper limit on the acceptable range that is automatically determined, thus avoiding an acceptable range from being set with an abnormally wide or narrow range.

With the scan device according to the first invention, the movement to the next measurement point happens basically when all conditions are satisfied. However, it is possible for the time required for all conditions to be met to become extremely long or for the conditions to be never met due to some failure no matter how much time is spent.

As a countermeasure for such situations, one preferable mode of the scan device according to the first invention calls for the scan control means to spatially move the sample or the measurement system or to change a physical condition so that a movement to the next measurement point forcibly happens if all conditions are not satisfied at a particular measurement point within a predetermined time.

By so doing, even if a measurement point exists where all conditions are not satisfied due to some abnormality or some failure, the overall time required for the measurement is prevented from becoming greatly extended. Furthermore, the reduction in measurement accuracy is confined only to those particular measurement points, and the measurements for almost all other measurement points are performed with a high accuracy.

As another preferable mode of a scan device according to the first invention, it is possible for the scan control means to be configured so that if all conditions for any one measurement point are not satisfied within a predetermined time, further scanning is suspended.

By so doing, if some abnormality or some failure causes the scanning to be impeded or a damage or failure of the measurement instrument itself is conceivable, the scanning and measurement can be stopped. This measure is effective in, for example, FM-AFM and other surface analysis instruments to prevent damages to the probe needle or the sample caused by the collision between the two. It is more preferable if, in addition to the stoppage of scanning and measurement, a fail-safe control is provided for increasing the separation distance between the probe needle and the sample.

Furthermore, if the scan device according to the first invention does not include a feedback control that accompanies the scanning, the scan device can further include a signal adding means that adds two or more types of signals that are acquired by the measurements at each measurement point with the n conditional decision means judging whether or not the values of two or more types of values added by said signal adding means at each measurement point exceeds a predetermined value defined for each in advance.

For example, an electron probe micro-analyzer independently detects, at each measurement point, X-rays and electrons including secondary electrons and backscattered electrons that are emitted from the sample. The X-ray strength signal and the electron strength signal can be used as the aforesaid two types of signals so that the system promptly moves to the next measurement point when the added value of the two signals exceeds a predetermined value.

By so doing, the measurement time is reduced for measurement points where the signal strength is relative high and the measurement time is conversely increased for measurement points where the signal strength is relatively low. Previously, the measurement time at all measurement points was set to be long so that a sufficient S/N ratio was obtained even from measurement points where the signal strength was low. However, with the afore-described configuration, because the movement to the next measurement point occurs immediately when a sufficient S/N ratio is obtained, the use of unnecessarily long measurement time is eliminated. As a result, measurement throughput is increased. Furthermore, because sufficient addition is performed for measurement points where the signal level is low, a sufficiently high S/N ratio is obtained, and measurements of a high precision are performed.

Even with a measurement instrument where scanning is not accompanied by a feedback control and where only one type of signal is acquired by the measurement at each measurement point, an added signal value can be used as described above to adaptively determine the measurement time.

To explain, to solve the afore-described problems, a scan device according to a second invention is a scan device for use with a measurement instrument which performs measurements by sequentially scanning each of a plurality of measurement points that are defined on a sample or a measurement instrument which performs measurements by sequentially scanning each of a plurality of measurement points defined in terms of a physical measurement condition, the scanning device including:

a) a signal addition means for adding the signals acquired by measurements at each measurement point;

b) conditional decision means for judging whether or not the added values by said signal addition means exceeds a predetermined value; and c) a scan control means which, if the conditional decision means judges that the added value has exceeded the predetermined value, spatially moves the sample or the measurement system or changes the physical condition so as to move to the next measurement point.

With the scan device according to the first invention or the second invention, no limitation is imposed on the "dimensions" of the scanning when a plurality of measurement points is sequentially scanned. To explain, the measurement points that are defined on a sample may be scanned 1-dimensionally, 2-dimensionally or 3-dimensionally, Furthermore, if measurement points that are defined in terms of a physical condition are scanned, the scan may be performed using more dimensions so a scan of 4 or more dimensions is conceivable.

Effects of the Invention

With the scan device according to the first invention and the second invention, the measurement time for each of the plurality of measurement points that are scanned sequentially is adaptively determined. Unlike the case where the measurement time is uniformly decided, there is no wasted measurement time. As a result, the amount of time required for performing the measurements at all of the many measurement points included in a predetermined area is greatly reduced as compared to the previous art, thus contributing to increasing the measurement throughput. Furthermore, even with scans that involve performing two or more feedback controls, measurements are performed after the two or more feedback control loops have fully stabilized, thus increasing the throughput while maintaining a high measurement accuracy.

BRIEF DESCRIPTION OF THE FIGURES

The patent or application file contains at least one drawing executed in color. Copies of this patent or patent application publication with color drawings will be provided by the Office upon request and payment of the necessary fee.

FIG. 18(a) shows an image that was obtained with a forward-direction scan and (b) shows an image that was obtained with a reverse-direction scan.

DESCRIPTION OF THE NUMERICAL REFERENCES

Figure 1:
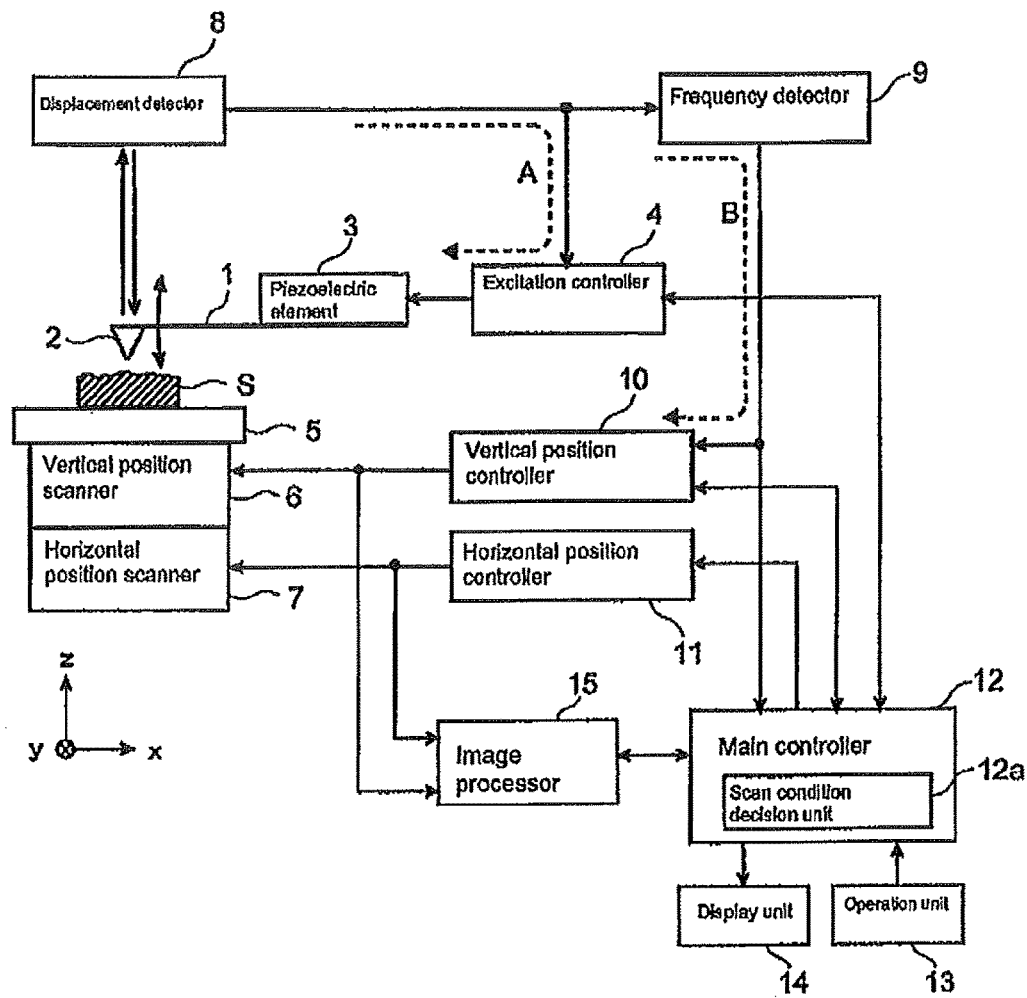
FIG. 1 is a schematic block diagram of an FM-AFM as an embodiment of a measurement instrument that uses a scan device according to the present invention.

1. Cantilever
2. Probe needle
3. Piezoelectric element
4. Excitation controller
5. Sample support pedestal
6. Vertical position scanner
7. Horizontal position scanner
8. Displacement detector
9. Frequency detector
10. Vertical position controller
11. Horizontal displacement controller
12. Main controller
12a. Scanning conditional decision unit
13. Operation unit
14. Display unit
15. Image processor
S. Sample
A, B, C. Feedback control loop
100. Two-dimensional area
101. Measurement point
101a. Measurement point start point
101b. Measurement end point
20. Controlled object
21. Detector
22. Error computation unit
23. Compensation controller
30. Lock-in amplifier
31. Alternating current voltage source
32. Adder
33. Potential controller
34. Direct current voltage source
41. Electron gun
42. Deflection coil
43. Objective lens
44. Sample stage
46. Stage drive mechanism
47. Sample stage controller
49. X-ray detector
50. X-ray analyzer
51. Amplifier
52, 57. AID converter
53. X-ray data processor
55. Electron detector
56. Imaging unit
58. Image data processor 59. Acceleration source
60. Central control processor
60a. Scanning conditional decision unit
61. Operation unit
62. Display unit

BEST MODE FOR PRACTICING THE INVENTION

A FM-AFM is described next with reference to figures as one embodiment of a measurement instrument that uses a scan device according to the present invention, FIG. 1 shows a schematic block diagram of the present embodiment as a FM-AFM.

A probe needle 2 is disposed at one end of cantilever 1 having the shape of a very small leaf spring and a length of, for example, approximately 100 to 200 μm. A piezoelectric element 3 serving as an excitation unit is disposed at the other end of the cantilever 1. The piezoelectric element 3 undergoes microscopic displacements based on a voltage that is applied by an excitation controller 4 and causes the cantilever 1 to vibrate at its resonant frequency. The cantilever 1 has a natural resonant frequency fr that is determined by factors such as its spring constant and mass of the probe needle 2.

Sample S, the measured object, is placed on a sample support pedestal 5 which is movable in a perpendicular direction (z-axis direction) by a vertical position scanner 6 and is movable in two-dimensional directions (x-axis direction and y-axis direction) within a horizontal plane by horizontal position scanner 7. While the probe needle 2 is being vibrated at its resonant frequency fr and at a predetermined amplitude, the probe needle 2 is brought close to the surface of sample S. This causes a dynamic interaction between the probe needle 2 and the surface of the sample S. This interaction changes the resonant frequency fr of the cantilever 1. The change that happens, that is, the frequency shift $\Delta f$, becomes a negative value if there is an attraction between the probe needle 2 and the surface of the sample S and becomes a positive value when there is a counterforce between the two.

A displacement detector 8 which detects the mechanical displacement of the probe needle 2 includes, for example, a light source, a photodetector whose detection face is divided into two or four and a computation circuit that performs computations on a plurality of detection signals from the photodetector. The displacement detection signals from the displacement detector 8 are input to the frequency detector 9 which performs FM demodulation on the displacement detection signals to detect the amount of change in the resonant frequency, that is, frequency shift $\Delta f$. The frequency detector 9 can be configured using, for example, various filters and a resonance circuit formed using a phase lock loop (PLL), inductors and capacitors.

Based on the displacement detection signals from the displacement detector 8, the excitation controller 4 applies a voltage to the piezoelectric element 3 so that the cantilever 1 vibrates at the aforesaid resonant frequency fr and at a constant vibration amplitude. To further explain, a feedback control loop A identified by the dotted line in FIG. 1 controls the vibration amplitude of the cantilever 1 so that it remains constant. To be more precise, the vibration amplitude is controlled so that it is equal to a control target value that is set by a main controller 12.

While in this state, when the vertical position scanner 6 moves the sample S in the z-axis direction to become close to the tip of the probe needle 2, the effective spring constant of the cantilever 1 is changed by the afore-described mechanical interaction between the probe needle 2 and the sample S, thus causing a change in the resonant frequency fr. Since this change appears as a change in the displacement quantity of the probe needle 2 (situated at one end of the cantilever 1), the frequency detector 9 detects the amount of change in the resonant frequency (frequency shift $\Delta t$) based on the displacement detection signals from the displacement detector 8 and feeds back the detection signals to the vertical position controller 10.

The vertical position controller 10 controls the vertical position scanner 6 and changes the distance (height in the z-axis direction) between the probe needle 2 and the sample S. A horizontal position controller 11 controls a horizontal position scanner 7 so that the sample S is moved in the direction of two axes, the x-axis and the y-axis, and the measurement points on the sample S are scanned by the probe needle 2. The vertical position controller 10 and the horizontal displacement controller 11 are both comprehensively controlled by the main controller 12. An operation unit 13 controlled by users and a display unit 14 capable of displaying two-dimensional images are connected to the main controller 12.

For example, to obtain concave/convex images of a predetermined two-dimensional area of the sample S, the vertical position controller 10 drives the vertical position scanner 6 and displaces the sample support pedestal 5 in the z-axis direction so that the frequency shift $\Delta f$ from the frequency detector 9 remains constant. In other words, the feedback control loop B identified by a dotted line in FIG. 1 controls the separation distance between the sample S and the tip of the probe needle 2 so that it remains constant. To be more precise, the separation distance is controlled so that it is equal to a target value that is set by the main controller 12.

Figure 2:
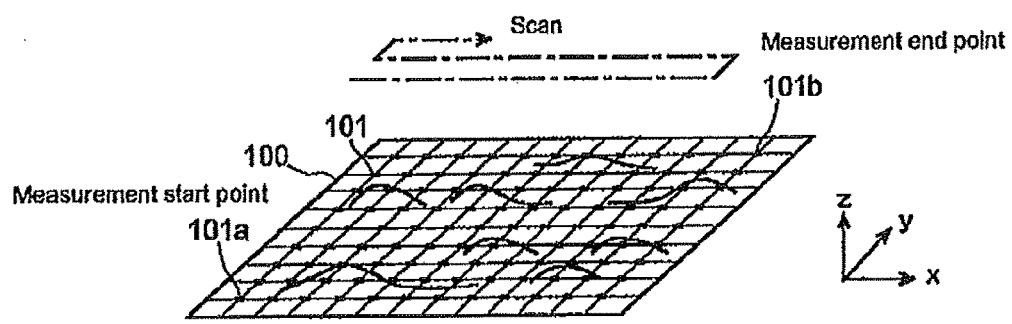
FIG. 2 is a conceptual view showing how a sample is scanned with the present embodiment in an FM-AFM.

The horizontal displacement controller 11 drives the horizontal position scanner 7 so that the points measured by the probe needle 2 move within the aforesaid predetermined two-dimensional area. Because the value of the displacement quantity $\Delta z$ in the z-axis direction changes depending on the concavity and convexity of the surface of sample S, an image processor 15 creates concave/convex images from the displacement quantities $\Delta z$ and the addresses set by the horizontal displacement controller 11 representing the positions on the sample S in the x-axis and y-axis directions. Specifically, as FIG. 2 shows, a plurality of measurement points 101 that are set in a grid-like pattern in a two-dimensional area 100 of a sample S is sequentially scanned to obtain a signal (displacement quantity $\Delta z$) at each measurement point. A concave/convex image of the two-dimensional area on the sample S can be displayed on the screen of a display unit 14.

Figure 3:
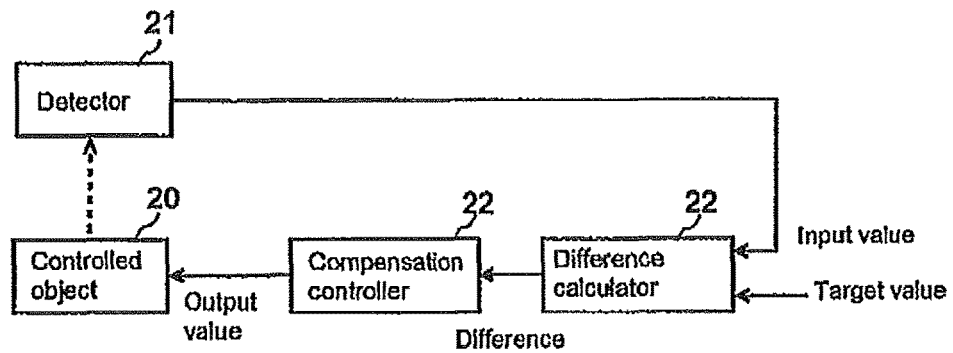
FIG. 3 is a block diagram showing the basic configuration used for feedback control.

FIG. 3 shows a block diagram of a basic configuration used for feedback control by, for example, the aforesaid feedback control loops A and B.

The output signal from the detector 21 which detects the displacement quantity of the controlled object 20 is input to an error computation unit 22 as its input value. A value representing the target value is also input to the error computation unit 22. The error computation unit 22 calculates the difference between the input value and the target value and supplies the difference quantity to a compensation controller 23. The compensation controller 23 adjusts the output value that is supplied to the controlled object 20 so that the difference quantity becomes zero. This keeps the displacement of the controlled object 20 to a predetermined amount. For example, with the aforesaid feedback control loop A, displacement detector 8 corresponds to detector 21, excitation controller 4 corresponds to error computation unit 22 and compensation controller 23, and piezoelectric element 3 corresponds to controlled object 20. With feedback control loop B, displacement detector 8 and frequency detector 9 correspond to detector 21, vertical position controller 10 corresponds to error computation unit 22 and compensation controller 23, and vertical position scanner 6 corresponds to the controlled object 20.

Figure 4:
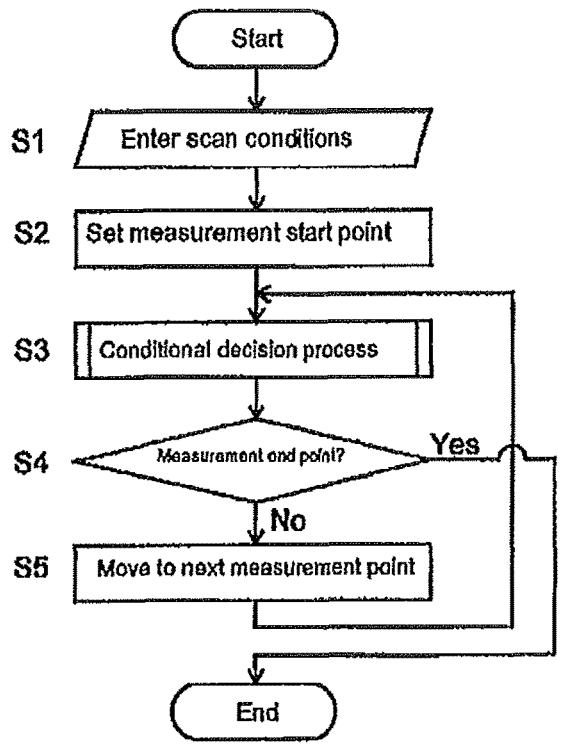
FIG. 4 is a flowchart showing the characteristic control and processing operations used for obtaining concave/convex images in the present embodiment in an FM-AFM.

The characteristic control and processing operations that are performed with the present embodiment in a FM-AFM for obtaining concave/convex images are described next with reference to the flowcharts shown in FIG. 4 through FIG. 11. FIG. 4 shows the flowchart for the main routine used for controlling and processing the scanning of the measurement points.

First, the operator uses, for example, an image that is captured by an optical camera not illustrated and the operation unit 13 to set a two-dimensional area where convex/concave images are to be obtained. The operator sets scanning conditions such as the distance between measurement points 101 in the x-axis direction and the y-axis direction (step S1). When doing this, it is also possible to set the acceptable range that is used as a decision criteria by the conditional decision processes described below. FIG. 2 shows one example of a scanning sequence, but it is possible to allow the operator to set a scan sequence. For example, in addition to sequentially scanning in the x-axis and the y-axis directions, it is possible to perform a rough scan of the entire two-dimensional area 100 that is specified in advance while skipping some of the measurement points that are located spatially adjacent and to follow the rough scan with a more detailed scan that fills in the measurement points that were skipped. In other words a variety of scanning algorithms can be used.

The main controller 12 starts the measurement when so instructed by the operator. First, the main controller 12 determines a measurement starting point 101a where scanning is to start within a two-dimensional area 100 and controls the horizontal displacement controller 11 so that the probe needle 2 is situated above the measurement start point 101a (step S2). Next, the main controller 12 executes a conditional decision process at the measurement point (step S3). A detailed description of the conditional decision process is provided later. When the conditional decision process is completed, a decision is made as to whether the measurement point is the measurement end point 101b which identifies the point for ending the scan (step S4). If the measurement point is not the measurement end point 101b, the horizontal displacement controller 11 is controlled so that the probe needle 2 is positioned at the next measurement point (step S5). Control then returns to step S2. On the other hand, if the measurement point is determined in step S4 as being the measurement end point, the measurement process is terminated.

Figure 5:
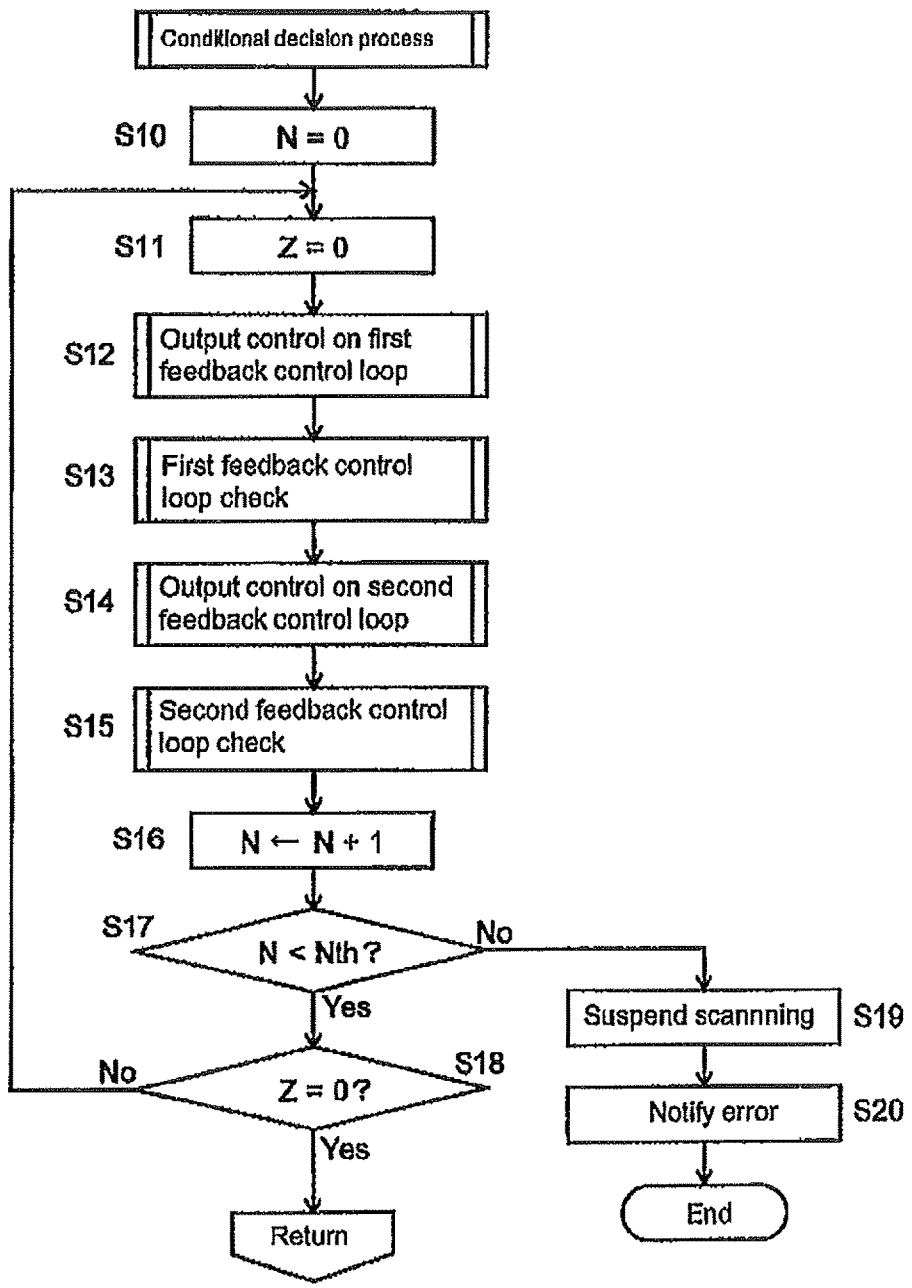
FIG. 5 is a flowchart showing the characteristic control and processing operations used for obtaining concave/convex images in the present embodiment in an FM-AFM.
Figure 6:
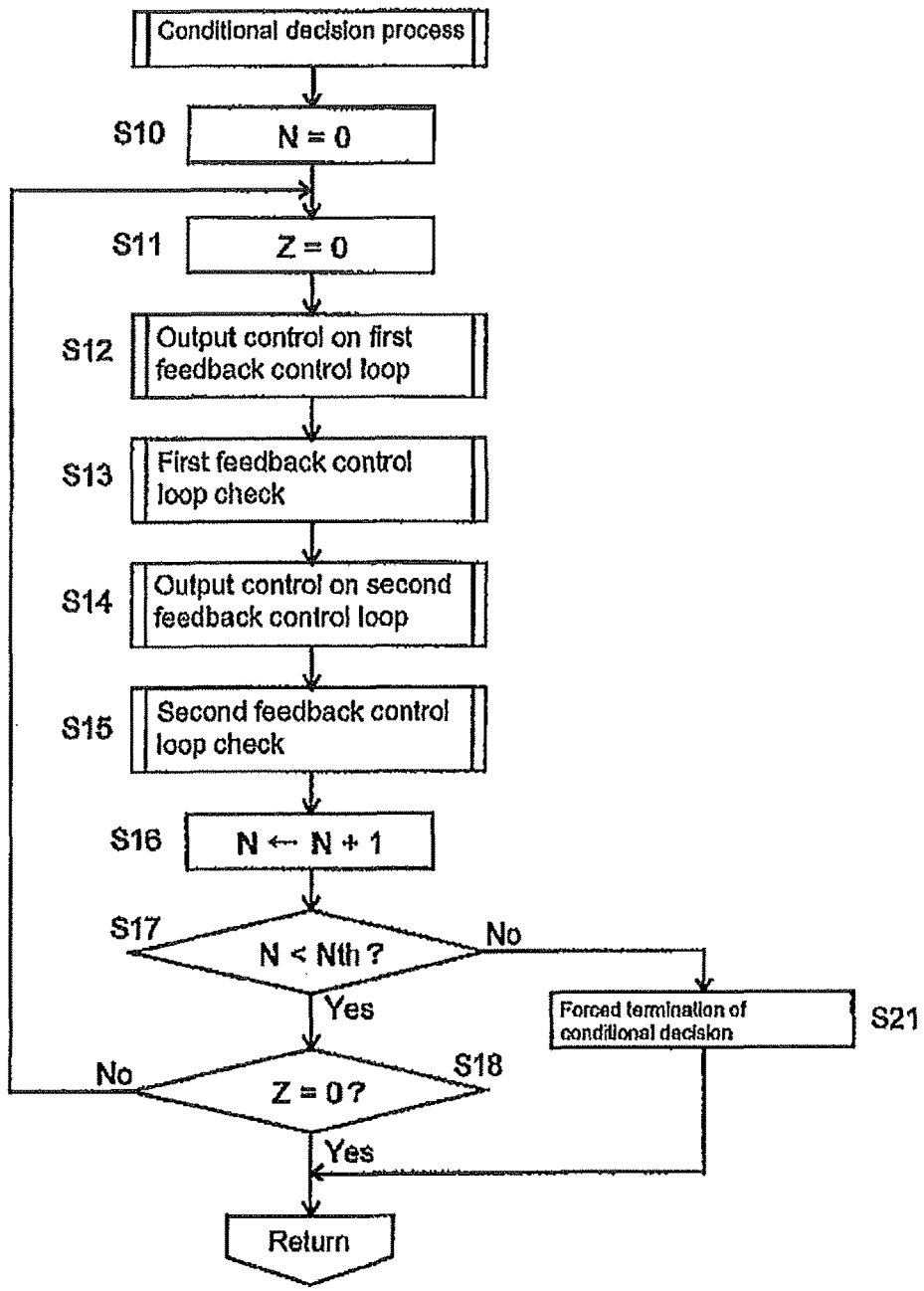
FIG. 6 is a flowchart showing the characteristic control and processing operations used for obtaining concave/convex images in the present embodiment in an FM-AFM.

FIG. 5 and FIG. 6 are flowcharts showing examples of subroutines that are used to execute specific procedures for performing the conditional decision processes performed in the afore-described step S3. The example of FIG. 5 is described first.

First, the scanning conditional decision unit 12a of the main controller 12 resets variable N used for counting the number of iterative counts (step S10) and also resets variable Z which is used for the conditional decision (step S11). Next, output control is executed on the first feedback control loop (step S12), and the first feedback control loop is checked (step S13). The first feedback control loop is used for controlling the aforesaid feedback control loop A which is used for keeping the vibration amplitude of cantilever 1 constant. Next, an output control is executed on the second feedback control loop (step S14), and the second feedback control loop is checked (step S15). Here, the second feedback control loop is used for controlling the aforesaid feedback control loop B which is used for controlling the separation distance between the probe needle 2 and the surface of the sample S. The detailed contents of how the output of these feedback control loops is controlled and how the feedback control loop is checked are described below. However, if some problem is encountered in the check of the feedback control loops in steps S13 and S15, a value of 1 is added to variable Z so that at least Z=0 does not hold.

Next, the value of variable N for counting the iterations is incremented by 1 (step S16). The value of variable N is checked as to whether it is less than the value of Nth, the upper limit value (step S17). The upper limit value Nth is determined by a variety of factors such as the response characteristics of the feedback control loop, the measurable range (such as the maximum concavity and convexity quantities of the sample surface) and the range of the spring constant of cantilever 1 that is used but can also be made to be modifiable and settable by the user (operator).

If the decision made in step S17 is that the value of variable N is less than the value of the upper limit value Nth, a decision is made as to whether or not the value of variable Z used for the conditional decision is 0 (step S18). As afore-described, since, if some problem is encountered when the feedback control loop is checked in steps S13 and S15, the value of the variable Z will not be 0, control returns from step S18 to step S11 if the value of Z is not equal to 0. The variable Z is reset, and the processes of steps S12 through S17 are executed. Hence, even if, in step S18, the value of variable Z used for conditional decision is not 0, steps S12 through S15 are repeated until the value of variable N for counting the iterations reaches the value of the upper limit value Nth. If, during that process, the value of variable Z used for the conditional decision becomes equal to 0 in step S18, that is, if no problems are encountered in the feedback control loop check performed in steps S13 and S15, the decision made in step S18 becomes "Yes." The conditional decision process is terminated, and control returns to the main routine.

On the other hand, if the decision made in step S17 is that the value of variable N for counting the iterations has reached the upper limit value Nth, the main controller 12 stops the scanning at that moment, and the vertical position scanner 6 is controlled to move the probe needle 2 away from the sample S and to avoid contact between the probe needle 2 and the sample S (step S19). Then, to inform the operator that the measurements have been suspended, the operator is informed of the error, for example, by a message that is displayed on the display unit 14 (step S20). However, if, despite repeating steps S12 through S15, the value of variable Z used for the conditional decision does not become 0 before the value of variable N for counting the iterations reaches the upper limit value Nth, that is, if both of the two feedback control loops do not check out as being OK, the measurements are suspended partway into the measurement process.

Another example of the conditional decision process is described with reference to FIG. 6. In the conditional decision process shown in FIG. 6, the control and processes performed in steps S10 through S18 are absolutely identical to those of the example shown in FIG. 5 except for the process that is performed when a decision of "No" is made in step S17. To explain, with the example shown in FIG. 5, if the value of variable N for counting the iterations is judged to have reached the upper limit value Nth, the scanning and measurement were suspended. However, with the example shown in FIG. 6, if the value of variable N for counting the iterations is judged to have reached the upper limit value Nth, the conditional decision process is forcibly terminated (step S21), and control returns to the afore-described main routine. This means that, for the particular measurement point that was being measured, the value for displacement quantity $\Delta z$ is acquired without at least either one of the two feedback control loops being checked out as being OK, and the system moves to the next measurement point. Even though the accuracy of the displacement quantity $\Delta z$ that is obtained without at least either one of the two feedback control loops checking out as being OK will be relatively low, so long as normal measurements are carried out at the other measurement points, the measurement results that are obtained will have a sufficiently high accuracy with respect to the overall two-dimensional area 100.

Figure 7:
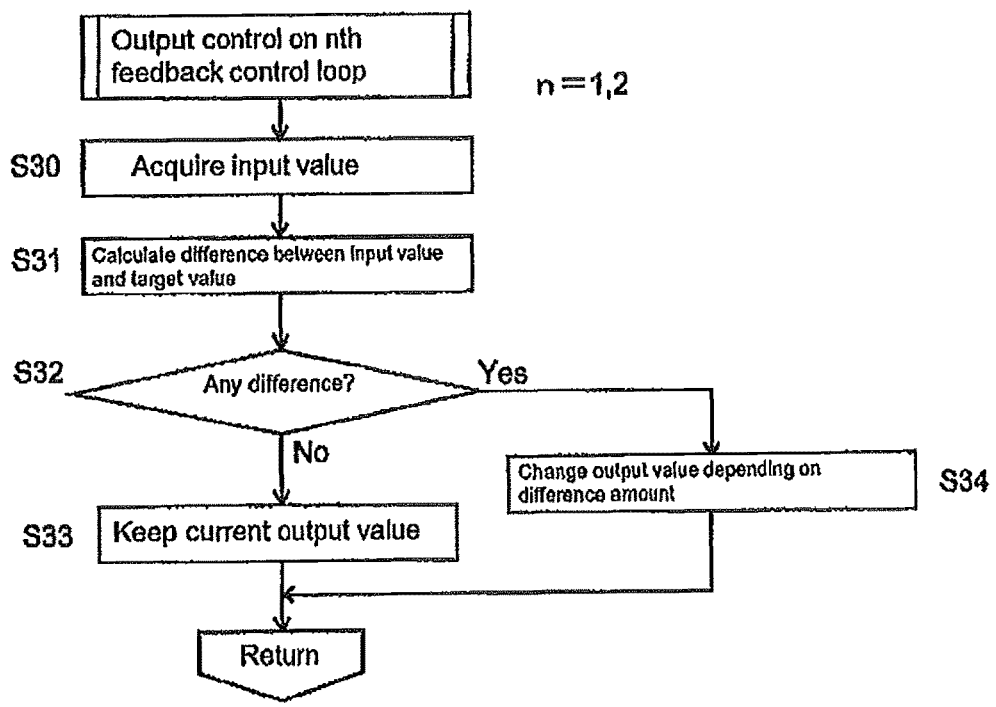
FIG. 7 is a flowchart showing the characteristic control and processing operations used for obtaining concave/convex images in the present embodiment in an FM-AFM.

Next, one example of a specific procedure that is used for controlling the output of the feedback control loop in steps S12 and S14 shown in FIG. 5 and FIG. 6 is described next with reference to FIG. 7. This output control is performed by error computation unit 22 and compensation controller 23 in the feedback control loop shown in FIG. 3. In FIG. 7, the value of n is either 1 or 2, and if n=1, step S12 is performed, and if n=2, step S14 is performed. This output control procedure is a very common feedback control procedure and is not a characteristic feature of the present invention.

First, the input value for the feedback control loop is obtained (step S30), and the difference between the input value and the target value is calculated (step S31). Whether or not there is a difference is determined (step S32), and if there is no difference, the output value is kept as is (step S33), this subroutine is terminated, and control returns to the routine shown in FIG. 4 or FIG. 5. If there is a difference, the output value is modified depending on the amount of the difference. The output value is usually changed so that the greater the difference quantity, the greater the change in the output value (step S34). A process such as this is used so that the controlled object 20 such as the piezoelectric element 3 or the vertical position scanner 6 is driven in a way that makes the input value approach the target value. The vibration amplitude of cantilever 1 converges to a constant value, and the separation distance between the probe needle 2 and the sample S also converges to a constant value.

Next, one example of a specific procedure that is used for checking the feedback control loop in steps S13 and S15 shown in FIG. 5 and FIG. 6 is described next with reference to FIG. 8 through FIG. 11.

Figure 8:
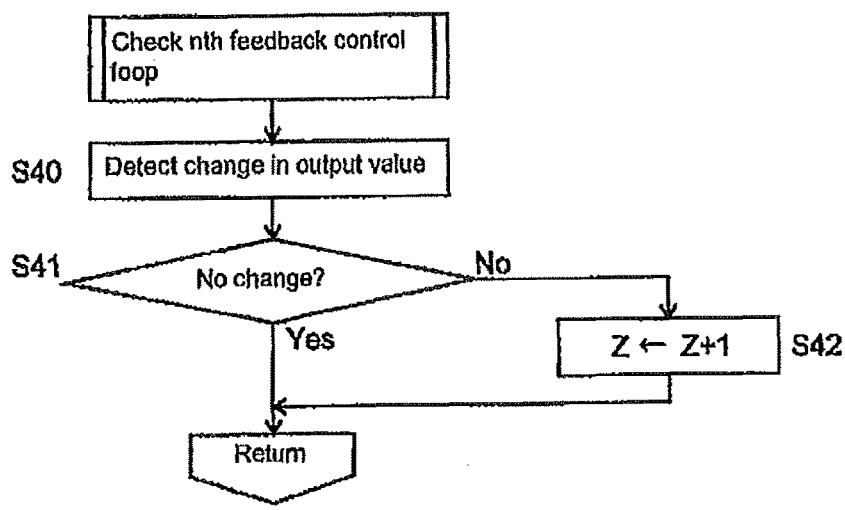
FIG. 8 is a flowchart showing the characteristic control and processing operations used for obtaining concave/convex images in the present embodiment in an FM-AFM.

The example of FIG. 8 is explained first. A scanning conditional decision unit 12a detects the change in the output value of the feedback control loop during a predetermined amount of time (step S40) and determines whether or not the change in the output value is substantially zero (step S41). If there is no change in the output value, this subroutine terminates, and control returns to the routine shown in FIG. 5 or FIG. 6, On the other hand, if there is a change in the output value, variable Z used for the conditional decision is incremented by one (step S42), and this subroutine terminates. In other words, with this example, when the output value of the feedback control loop converges to a value and does not change any more, the value of variable Z used for the conditional decision is set to zero, meaning that the scanning condition required for moving to the next measurement point is deemed to have been satisfied.

Figure 9:
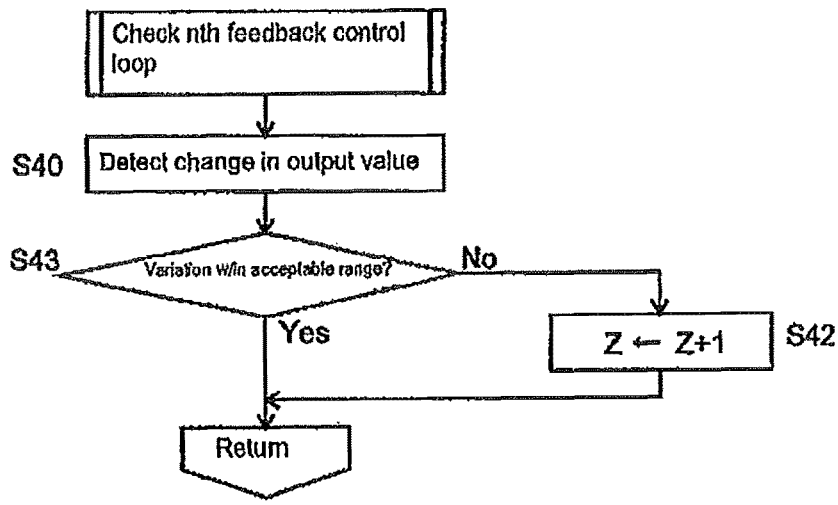
FIG. 9 is a flowchart showing the characteristic control and processing operations used for obtaining concave/convex images in the present embodiment in an FM-AFM.

The example of FIG. 9 is explained next. The scanning conditional decision unit 12a detects the change in the output value of the feedback control loop during a predetermined amount of time (step S40) and determines whether or not the change in the output value falls within a predetermined acceptable range defined in advance (step S43). If the change in the output value falls within the acceptable range, this subroutine is terminated, and control returns to the routine shown in FIG. 5 or FIG. 6. On the other hand, if the change in the output value is outside of the acceptable range, the variable Z used for the conditional decision is incremented by one (step S42), and this subroutine is terminated. In other words, with this example, if the output value of the feedback control loop converges to within the acceptable range, the value of variable Z used for the conditional decision is set to 0, meaning that a judgment is made that the scanning condition required for moving to the next measurement point has been met. Because the conditions that are used are more lax than those used in the example shown in FIG. 7, the measurements may possibly be less accurate, but the measurement time at each of the measurement points is reduced.

Figure 10:
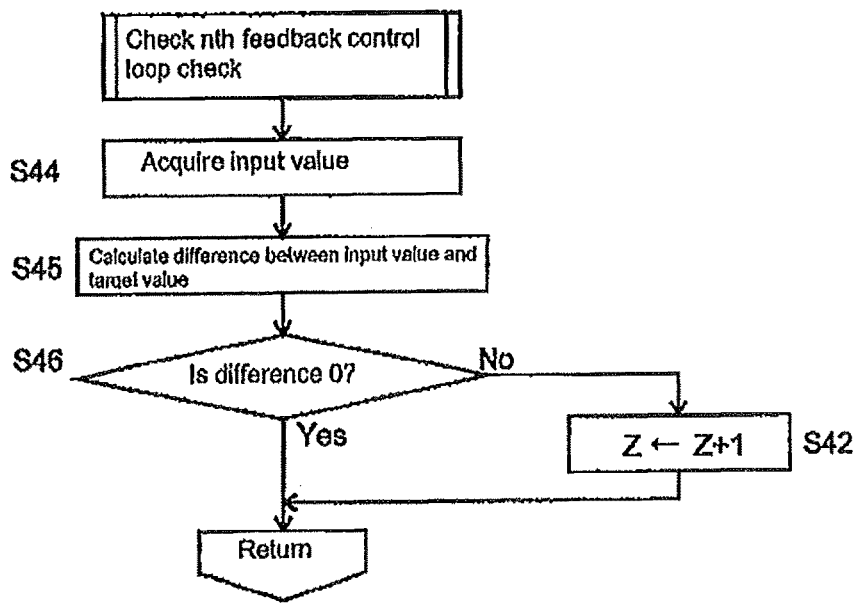
FIG. 10 is a flowchart showing the characteristic control and processing operations used for obtaining concave/convex images in the present embodiment in an FM-AFM.

The example shown in FIG. 10 is explained next. The scanning conditional decision unit 12a detects the input value to the feedback control loop at that moment (step S44) and calculates the difference between the input value and the target value (step S45). A decision is then made as to whether or not the difference is substantially zero (step S46). If the difference is zero, this subroutine is terminated, and control returns to the routine shown in FIG. 4 or FIG. 5. On the other hand, if the difference is not zero, the value of variable Z used for the conditional decision is incremented by one (step S42), and this subroutine terminates. What this means is that, with this example, just as with the example shown in FIG. 8, if the output value of the feedback control loop converges to a certain value and does not vary thereafter (that is, if the feedback control loop has completely stabilized), the value of variable Z used for the conditional decision is set to 0, meaning that a decision is made that the scanning conditions required for moving to the next measurement point have been met.

Figure 11:
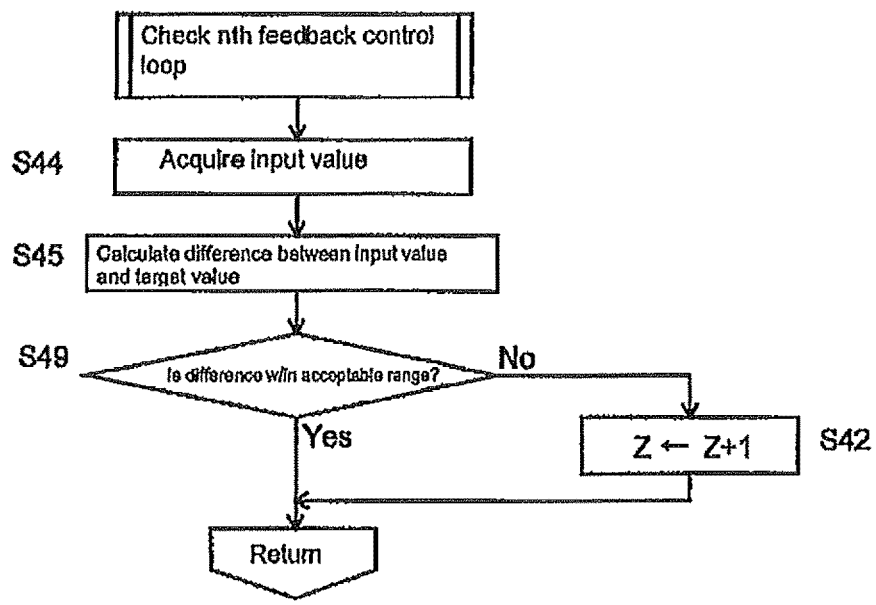
FIG. 11 is a flowchart showing the characteristic control and processing operations used for obtaining concave/convex images in the present embodiment in an FM-AFM.

The example shown in FIG. 11 is explained next. The scanning conditional decision unit 12a detects the input value to the feedback control loop at that moment (step S44) and calculates the error between the input value and the target value (step S45), A decision is then made as to whether or not the difference falls within a predetermined acceptable range set in advance (step S43). If the error falls within the acceptable range, this subroutine is terminated, and control returns to the routine shown in FIG. 4 or FIG. 5. On the other hand, if the difference falls outside the acceptable range, the value of variable Z used for the conditional decision is incremented by one (step S42), and this subroutine terminates. What this means is that, with this example, just as with the example shown in FIG. 9, when the output value of the feedback control loop converges to within a certain acceptable range, the value of variable Z used for the conditional decision is set to 0, meaning that a decision is made that the scanning conditions required for moving to the next measurement point have been met. Because the conditions that are used are more lax than those used in the example shown in FIG. 10, the measurements may possibly be less accurate, but the measurement time at each of the measurement points is reduced.

Any of the afore-described examples may be used for checking any of the feedback control loops, However, to avoid a situation where the value of variable N reaches the upper limit value Nth and time runs out in the afore-described step S17, it is better to use the example shown in either FIG. 9 or FIG. 11.

Regardless, if the conditions used for checking both feedback control loops A and B are met, i.e., if the decision is "Yes" in either step S41, S43, S46 or S49, the value of variable Z used for the conditional decision is not incremented, and a decision is made in step S18 that the value of the variable Z is zero. The result of this is the termination of the measurement for the particular measurement point, and the system moves to the next measurement point. Stated simply, when the vibration amplitude of cantilever 1 with probe needle 2 located above a measurement point converges to a predetermined state and when the separation distance between the probe needle 2 and the sample S converges to a predetermined state, the horizontal position scanner 7 is driven so that the system promptly moves to the next measurement point. This means that the measurement time at a measurement point becomes shorter as the time required for satisfying the two afore-described conditions becomes shorter.

Generally speaking, in moving from one measurement point to the next measurement point, the greater the change in the surface height of the sample S, i.e., the greater the concavities and convexities, the longer the time required for the afore-described feedback controls to fully converge. This means that the measurement time required at one measurement point becomes shorter where the sample surface is relatively flat, meaning that the scanning speed is increased. Where the concavities and convexities of the sample surface are large, the measurement time required for any one measurement point becomes longer, meaning a decreased scanning speed. With a conventional FM-AFM where a constant measurement time is used, the measurement time has to be defined with a long measurement time in mind. However, with a FM-AFM of present embodiment, the movement from one measurement point to the next measurement point at many measurement points occurs in a shorter measurement time, thus achieving the goal of achieving a large reduction in the time required for scanning the entire two-dimensional area and increasing the measurement throughput.

Furthermore, because, where the concavities and convexities of the sample surface are large, a sufficiently long measurement time is secured for any one measurement point, the result of the measurement ($\Delta z$) for a measurement point is obtained after vibration amplitude control and distance control had a chance to fully function for that measurement point, thus providing measurement results of a high accuracy.

Furthermore, by using a routine such as that shown in FIG. 5, if a problem in the measurement system makes normal feedback control impossible, the scanning and measurement can be suspended, thus avoiding more serious problems caused by, for example, damages due to contact between the probe needle 2 and sample S.

Figure 12:
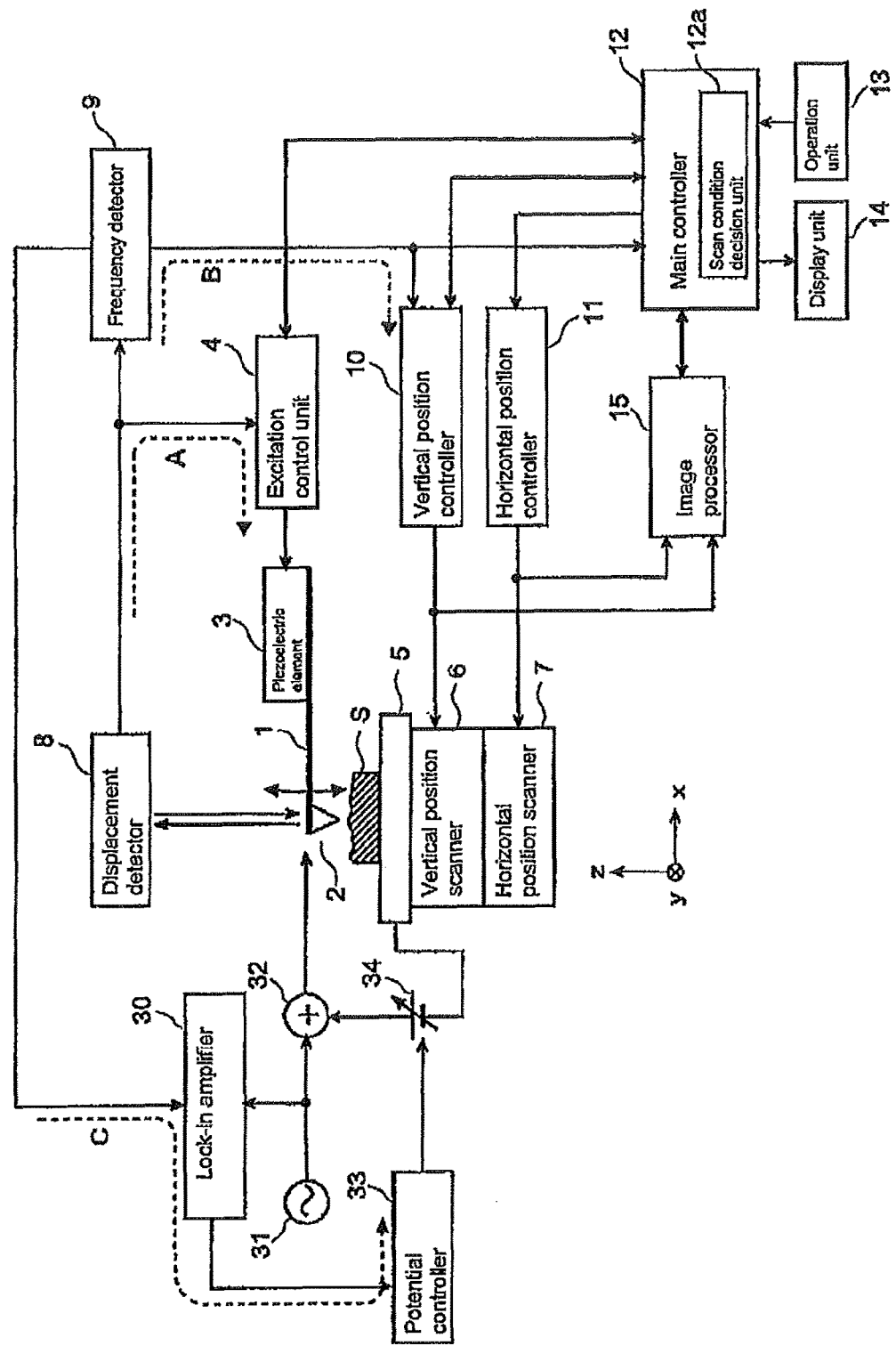
FIG. 12 shows a schematic diagram of a KFM as an embodiment of a measurement instrument that uses a scan device according to the present invention.

The afore-described embodiment discussed the case where two feedback control loops were used for the scanning. However, this number can be 3 or more. FIG. 12 shows a schematic view of another measurement instrument, a KFM, where the scan device according to the present invention is used. The same reference numbers are used in FIG. 12 for the same component elements as in the FM-AFM shown in FIG. 1. With the KFM, in addition to the afore-described controls for separation distance and vibration amplitude, a feedback control loop C is added to control the potential difference across probe needle 2 and sample S.

To explain, a voltage that is equal to the sum of DC offset voltage $V_{DC}$ created by the direct current voltage source 34 and an AC bias voltage from an alternating current voltage source 31 having a predetermined frequency $f_{AC}$ added by adder 32 is applied across the probe needle 2 and the sample support pedestal 5. This creates an electrostatic attraction between the probe needle 2 and the sample S. The displacement detector 8 detects the displacement of cantilever 1 caused by the electrostatic attraction and provides a detection signal to a lock-in amplifier 30. The lock-in amplifier 30 extracts the frequency $f_{AC}$ component of the AC bias voltage from the detection signal and sends the frequency $f_{AC}$ component to the potential controller 33. The potential controller 33 controls the direct current voltage source 34 and varies the DC offset voltage $V_{DC}$ so that the signal representing the frequency $f_{AC}$ component becomes zero. The DC offset voltage $V_{DC}$ when the frequency $f_{AC}$ component signal becomes zero is adopted as the potential value. The potential values are obtained for each of the measurement points to create a potential image for the sample S.

As afore-described, even if a greater number of feedback control loops is used, the basic control and processing operations for scanning remain the same as those for the afore-described embodiment. The only difference is the addition of an output control on the third feedback control loop and the addition of a step for checking the third feedback control loop following the processes performed in steps S12 through S15 in FIG. 5 or FIG. 6. In general, the response characteristics of the feedback control loop used for controlling the potential in a KFM is slower than the response characteristics of the other two feedback control loops. Hence, the measurement time at each measurement point becomes longer, and the time required for measuring the entire targeted two-dimensional area becomes longer.

Figure 17:
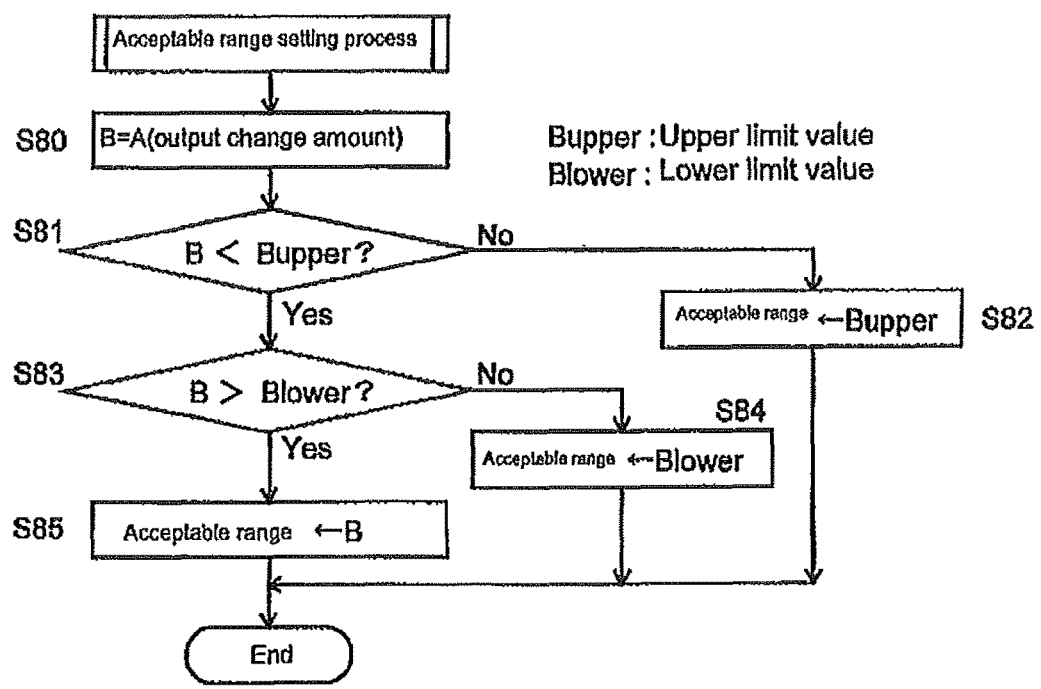
FIG. 17 is a flowchart showing the characteristic control and processing operations used for obtaining concave/convex images in the other embodiment as a KFM.

With the afore-described embodiment, the user was allowed to define from the operation unit 13 the acceptable range to be used in detecting differences and changes in the output value used for checking the feedback control loop. However, it is possible to add a function for automatically calculating and setting the appropriate acceptable range. FIG. 17 shows one example of a flowchart that can be used by the main controller 12 for executing a procedure for setting the range.

To explain, with each feedback control loop, the difference between the output value from the feedback control loop for the one earlier measurement point (the output value immediately before moving to the next measurement point) and the output value of the feedback control loop for the measurement point that was two earlier is determined as the amount of change. The inverse of the difference is multiplied by a constant A to calculate value B (step S80). This means that value B is inversely proportional to the amount of change in the output values. This value of B is basically adopted as the acceptable range, but it for example, the amount of change in the output values is 0, it's inverse will be infinity. This means that value B can be too large or too small and be inappropriate for use as an acceptable range. To avoid this situation, if value B exceeds a predefined upper limit value $B_{upper}$ ("No" in step S81), value B is set to the upper limit value $B_{upper}$ (step S82), and conversely if value B is less than a predefined lower limit value $B_{lower}$ ("No" in step S83), value B is set to the lower limit value $B_{lower}$ (step S84). If value B falls between the upper limit value $B_{upper}$ and the lower limit value $B_{lower}$, value B is used as is as the acceptable range (step S85).

Instead of adopting the difference in the output values from the feedback control loop from one measurement point previous and two measurement points previous as the amount of change, it is possible to use the difference in the output values from the feedback control loop from one or more measurement point previous and two or more measurement points previous as the amount of change. Furthermore, the amount of change can be derived using output values from the feedback control loop for 3 or more measurement points. Still furthermore, the amount of change can be derived using a mean or variance of such values.

By establishing the acceptable range used in the conditional decision in the afore-described manner, if the change in the output value of the feedback control loop from the immediately previous measurement point is small, the acceptable range can be made to be relatively large, thereby avoiding scanning from being suspended due to an external disturbance such as noise. If the change in the output value from the feedback control loop from the immediately previous measurement point is large, the acceptable range can be made relatively narrow for a more rigorous conditional decision.

Figure 13:
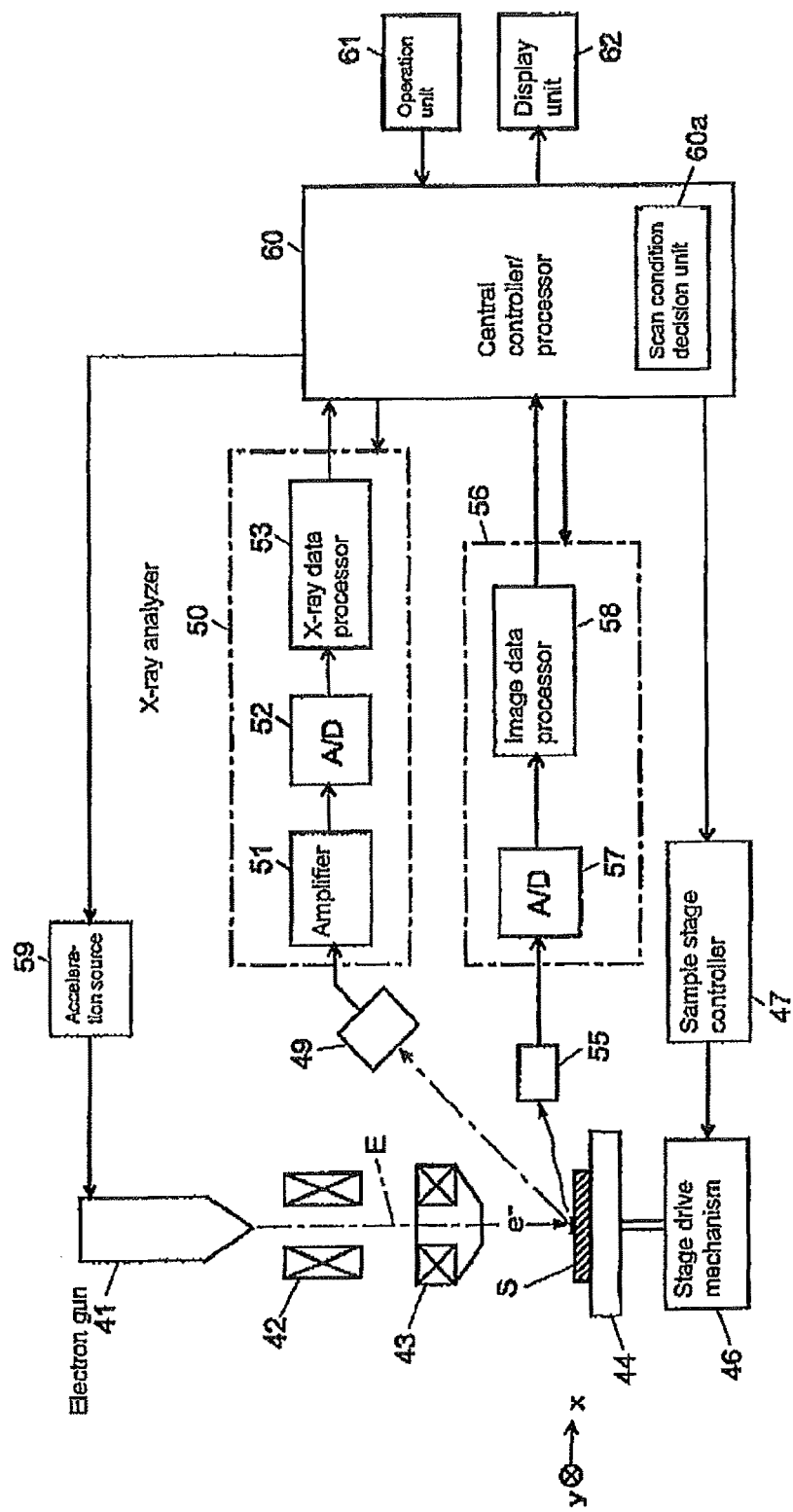
FIG. 13 shows a schematic view of the major components of an electron probe micro-analyzer as another embodiment of a measurement instrument that uses a scan device according to the present invention.

The afore-described embodiment pertains to the case where scanning is accompanied by a feedback control. However, described next is an example of the use of the present invention to a measurement instrument where scanning is not accompanied by a feedback control. As an example of such an instrument, an electron probe micro-analyzer is described next with reference to figures. FIG. 13 is a schematic view of the main components of an embodiment of the present invention in an electron probe micro-analyzer.

An electron beam E emitted by an electron gun 41 that is driven by an acceleration source 59 is converged by objective lens 43 after traveling through deflection coils 42 and is irradiated onto sample S that is placed on a sample stage 44. The sample stage 44 is movable under the control of a sample stage controller 47 in the x-axis and y-axis directions by means of a stage drive mechanism 46 that includes a motor and the like. This movement changes the irradiation position of the electron beam E on the sample S, that is, the measurement point is moved. The characteristic X-rays that are emitted from the sample S due to the irradiation with the electron beam E are input to an energy dispersive type X-ray detector 49 which then generates a pulse signal whose peak value is proportional to the energy level of the X-rays that are incident to it. The pulse signal is amplified by an amplifier 51 and converted into digital data by an A/D converter 52. The digital data is then input to an X-ray data processor 53. The X-ray data processor 53 separates and counts the number of X-ray pulses according to pulse height and stores the X-ray pulse counts as X-ray data.

The irradiation by the electron beam E also causes secondary electrons and backscattered electrons to be emitted from sample S which are detected by an electron detector 55 that includes a scintillator and a photomultiplier tube. The detection signal from the electron detector 55 is converted to a digital data by an A/D converter 57 and is input to an image data processor 58. The image data processor 58 creates a secondary-electron image (or a backscattered electron image) of an area of the sample surface corresponding to the irradiation position that is scanned by the electron beam E.

A central control processor 60 controls the operation of an X-ray analyzer 50 which includes an amplifier 51, A/D converter 52 and X-ray data processor 53, the operation of an imaging unit 56 which includes an A/D converter 57 and an image data processor 58, and the operation of a sample stage controller 47 and the acceleration source 59. The central control processor 60 includes a scanning conditional decision unit 60a which is the equivalent of the scanning conditional decision unit 12a in the afore-described embodiment.

With the electron probe micro-analyzer, secondary-electron images and X-ray images (mapping images) are simultaneously acquired in the following way. When the operator defines the measurement area on the sample S and the measurement conditions (including the scanning conditions) from the operation unit 61 and instructs that measurements be started, the central control processor 60 sends predetermined control signals to the sample stage controller 47 and the acceleration source 59. This causes the sample stage 44 to move so that the electron beam E strikes the measurement starting point on the sample S. An electron beam E having a predetermined energy level is emitted from the electron gun 41, and the scanning of the irradiated position of the electron beam E is begun. To further explain, the two-dimensional movement of the sample stage 44 caused by a stage drive mechanism 46 results in the irradiated position of the electron beam E to scan as shown in FIG. 2.

When the irradiated position of the electron beam E starts to scan, the central control processor 60 starts the operation of the X-ray analyzer 50 and the imaging unit 56. This causes the X-ray analyzer 50 to start acquiring data that corresponds to the energy level of the X-ray photons that are incident to the X-ray detector 49. Meanwhile, at the imaging unit 56, electron strength signals are sequentially acquired from each measurement point. In this way, X-ray data and electron strength data are sequentially obtained from each measurement point. When the irradiated position of the electron beam E reaches the measurement end point, the sample stage controller 47 sends a scan termination signal to the central control processor 60. This causes the acceleration source 59 to stop the irradiation of the electron beam E. Secondary electron images and X-ray mapping images of the targeted measurement area are obtained in this way and are displayed on the display unit 62.

Figure 14:
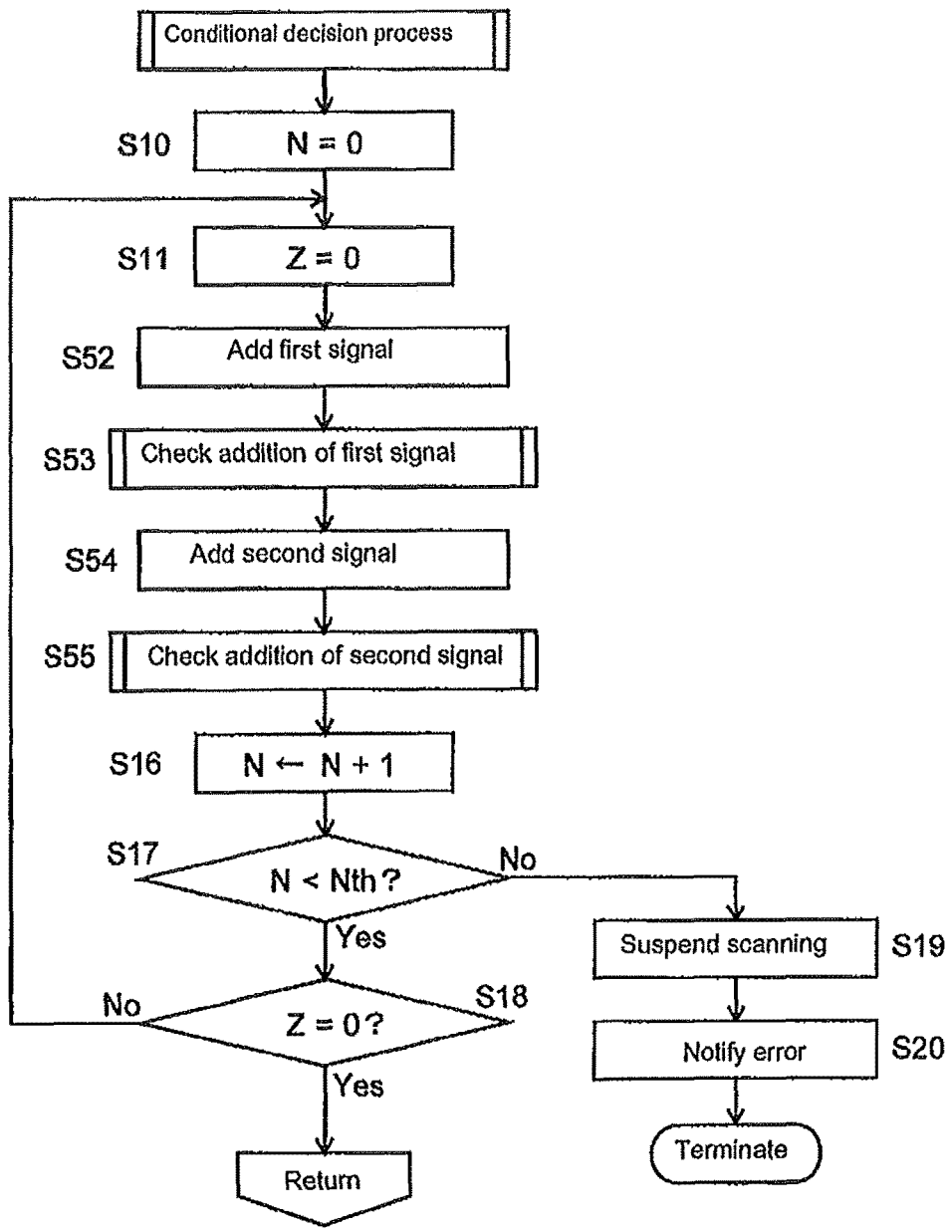
FIG. 14 is a flowchart showing the characteristic control and processing operations used for obtaining concave/convex images in the other embodiment as a KFM.
Figure 15:
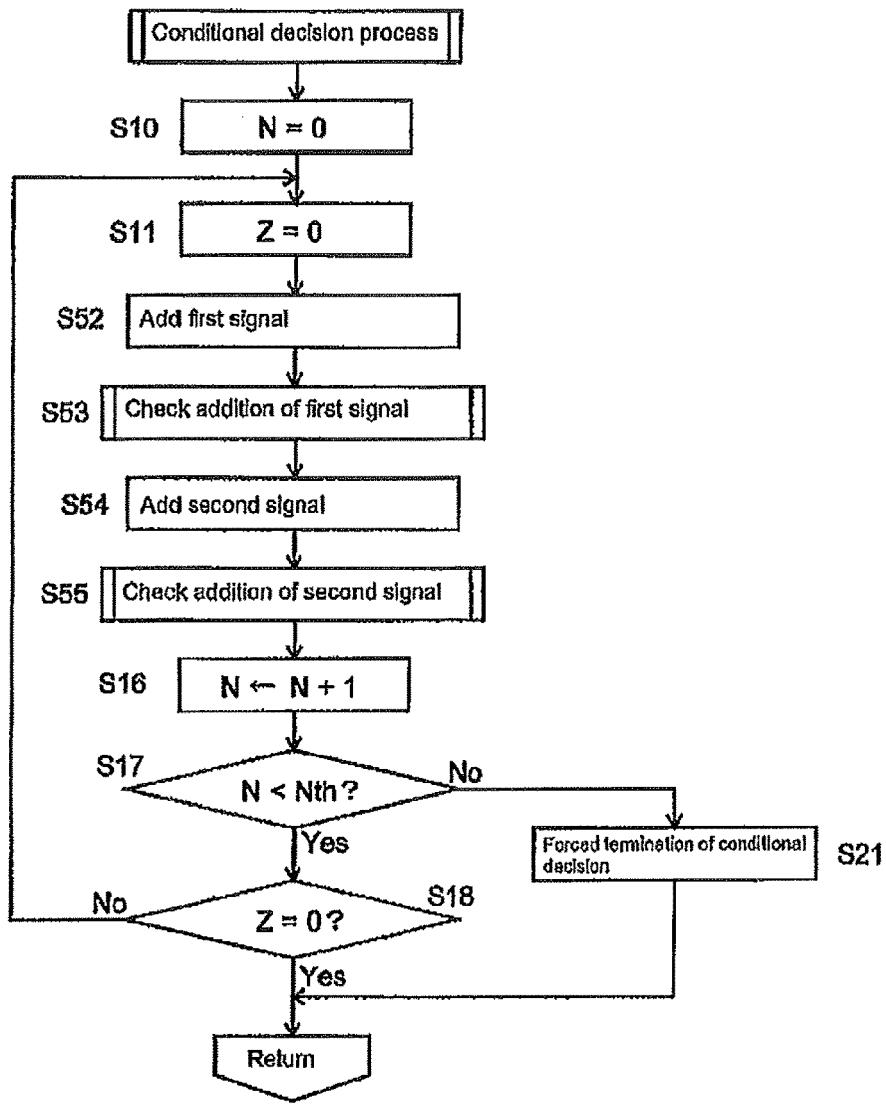
FIG. 15 is a flowchart showing the characteristic control and processing operations used for obtaining concave/convex images in the other embodiment as a KFM.

Just as with the afore-described embodiment, the electron probe micro-analyzer scans the respective measurement points following the procedure shown in FIG. 4 except for the conditional decision made in step 53. Instead of the processes shown in FIG. 5 or FIG. 6, the conditional decision process shown in FIG. 14 or FIG. 15 is performed. To explain, instead of performing an output control (steps S12 and S14) on the outputs of the first and second feedback control loops, the first and second signals are added (step S52, S54), and instead of checking the first and second feedback control loops (step S13 and S15), addition checks (step S53 and S55) are performed on the first and second signals where the first signal is the X-ray data and the second signal is the electron strength data.

As an example, consider the case where the subroutine shown in FIG. 14 is executed as the conditional decision process in step S3. In this case, the scanning conditional decision unit 60a first resets variable N used for counting the iterations and variable Z used for the conditional decision (steps S10 and S11) and then starts the addition of the X-ray data as the first signal that was obtained from the particular measurement point (step S52). Needless to say, the added value is reset to 0 before this process is started for the first time for any given measurement point. The scanning conditional decision unit 60a then continues to perform an addition check on the first signal (step S53).

Figure 16:
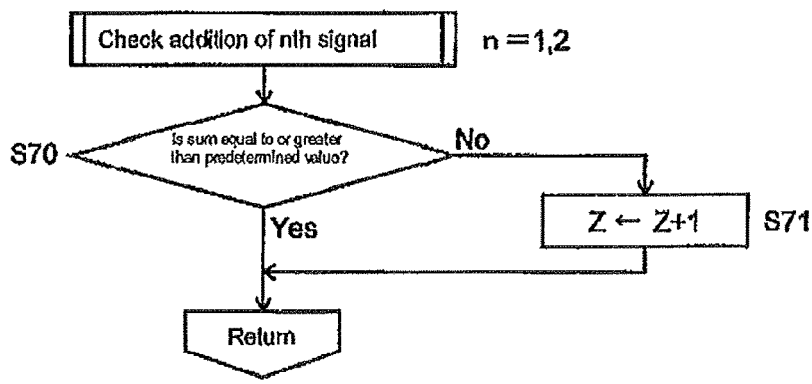
FIG. 16 is a flowchart showing the characteristic control and processing operations used for obtaining concave/convex images in the other embodiment as a KFM.

As FIG. 16 shows, in the addition check subroutine for the nth signal (n=1, 2 in this example), a decision is made as to whether or not the sum is equal to or greater than a predetermined value set in advance (step S70). If it is not equal to or greater than the predetermined value, variable Z for the conditional decision is incremented by 1 (step S71), this subroutine is terminated, and control returns to the conditional decision routine. On the other hand, if the sum is equal to or greater than the predetermined value, the subroutine is run until it ends, and control returns to the conditional decision routine. The addition (step S54) of the secondary electron strength data that is obtained from a particular measurement point as the second signal and the addition check (step S55) on the second signal are performed in a similar way.

This means that if the sum of the first signal and the sum of the second signal both become equal to or greater than the predetermined values, a decision is made in step S18 that the value of variable Z for the conditional decision is 0, the conditional decision subroutine is terminated, and control returns to the main routine. In other words, an instruction is issued to the sample stage controller 47 to stop the measurement at the particular measurement point and to move to the next measurement point. The stage drive mechanism 46 then moves the sample stage 44. This means that measurements are performed using a relatively short measurement time for measurement points where the signal level of the signal that is obtained is high. The measurements are performed using a relatively long measurement time for measurement points where the signal level of the signal that is obtained is low. The system then moves to the next measurement point. This means that measurements are not performed using a measurement time that is longer than necessary for a given measurement point, improving the measurement throughput. Furthermore, since the number of times that the signals are added is increased for measurement points where the signal level is low, the S/N ratio is improved over the previous systems.

In this way, even in the absence of a feedback control on the scanning of measurement points, the signals that are obtained from the measurements are used to adaptively adjust the scanning speed, thus improving the measurement throughput. Needless to say, it should be clear that a similar procedure can be used even when the number of types of signals that are obtained is 3 or more.

Both of the afore-described embodiments pertained to a measurement instrument where measurements were obtained for measurement points which were defined to be spatially different points on a sample. However, the measurement points need not be spatially defined and may instead be defined in terms of physical measurement conditions (measurement parameters) that affect the measurement results.

For example, with spectrum analyzers, network analyzers and the like, frequency is used as a measurement condition, and measurements are taken at each frequency while varying the frequency over a plurality of frequency levels. In this case, each of the respective frequencies can be considered as a measurement point. Also, with, for example, ultraviolet-visible spectrophotometers, infrared spectrophotometers, fluorophotometers and the like, the wavelength of light can be used as a measurement condition that is varied over a plurality of wavelengths as measurements are taken at each wavelength. In this case, each of the respective wavelengths can be considered as a measurement point.

EMBODIMENTS

Figure 18:
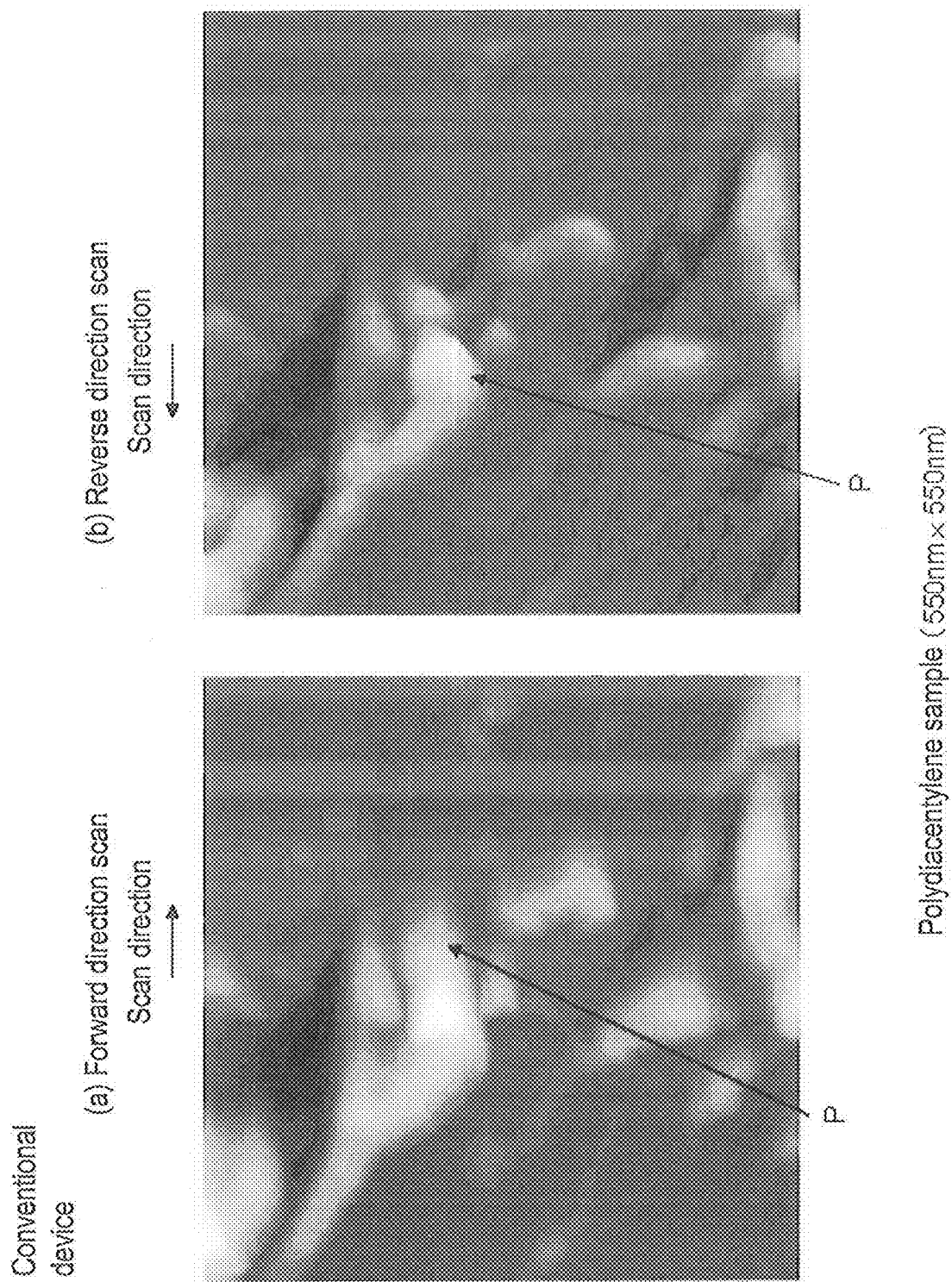
FIG. 18 shows examples of concave/convex images obtained using a conventional FM-AFM.

To elucidate the effects and the advantages of the FM-AFM of the present embodiment, the embodiments as FM-AFM according to the present invention and previous FM-AFM are compared next based on experimental results. FIG. 18 shows examples of concave/convex images obtained with a previous FM-AFM. FIG. 18(a) shows an image that was obtained when scanning in the forward direction (from left to right in the figure), and FIG. 18(b) shows an image obtained when scanning in the reverse-direction (from right to left in the figure). It is clear from the blurred images that feedback control (distance control) had not stabilized enough during the prescribed measurement time in areas with large concavities and convexities.

Figure 19:
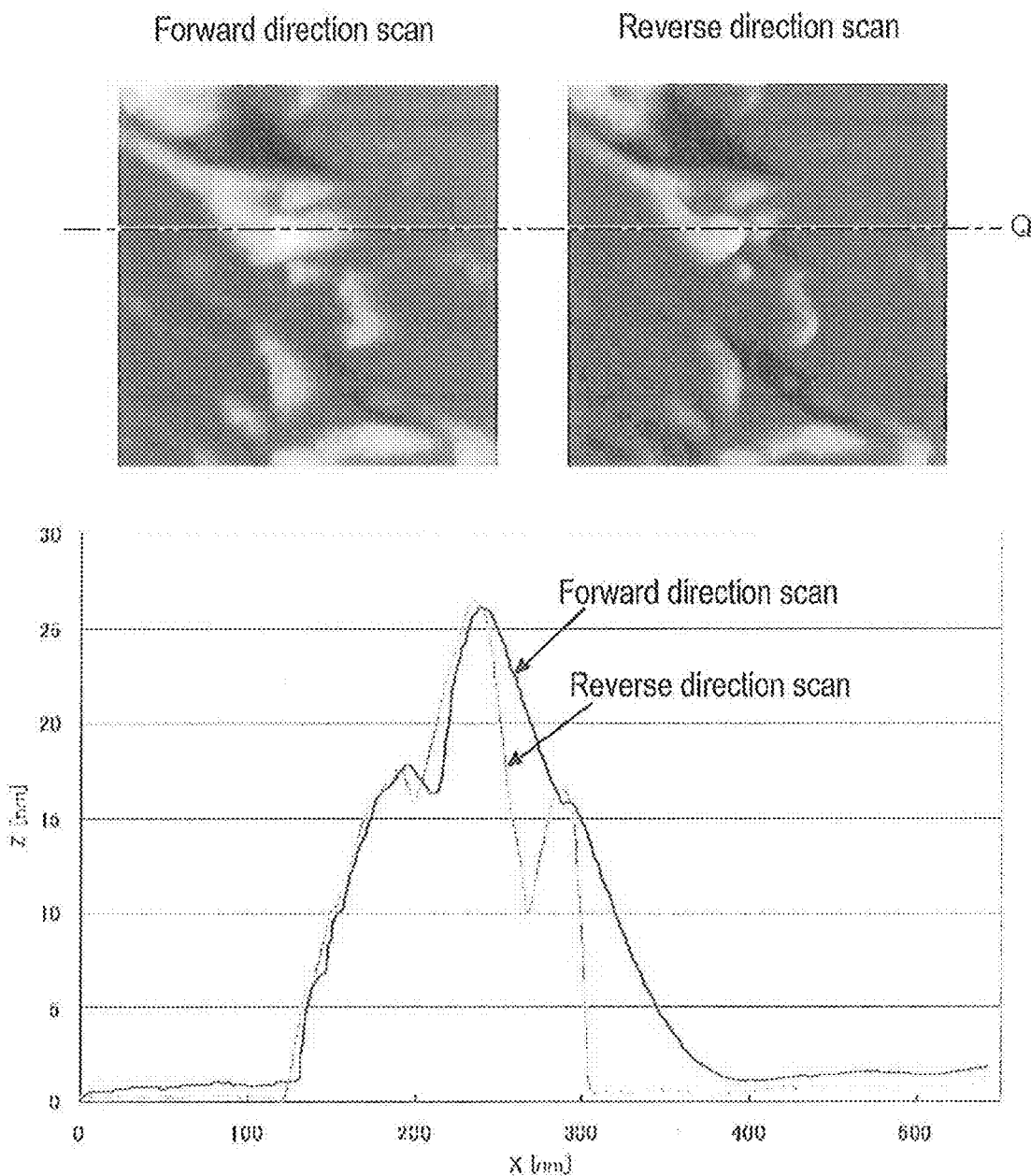
FIG. 19 is a graph showing values of sample height z obtained with a conventional FM-AFM at the position of line Q.

FIG. 19 shows a graph of the actual measurement values of sample height z obtained with a previous FM-AFM at line Q. It is clear that a large difference exists at some points in the actually measured sample heights between the forward-direction scan and the reverse-direction scan. The measurement points where the difference is large is where the feedback control (separation distance control) had not fully stabilized.

Figure 20:
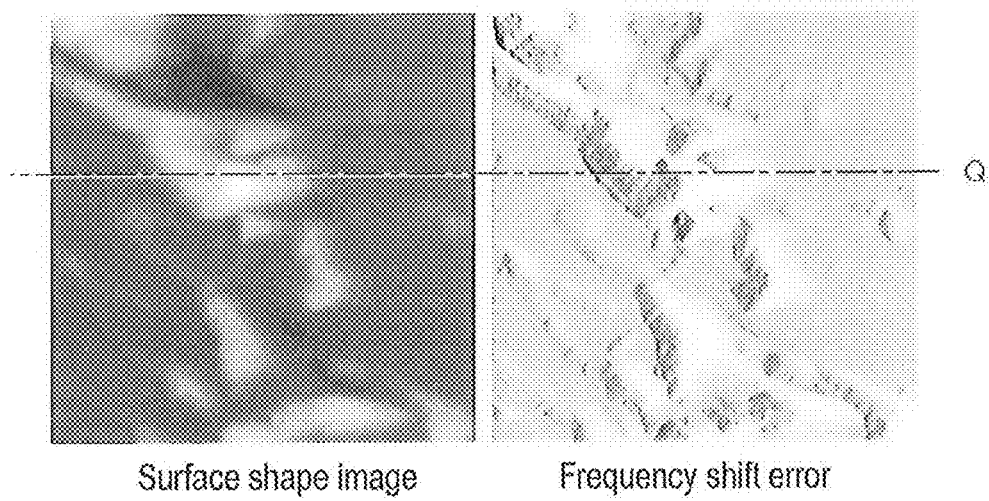
FIG. 20 is a graph showing frequency shift error with a forward-direction scan using a conventional FM-AFM at the position of line Q.
Figure 20:
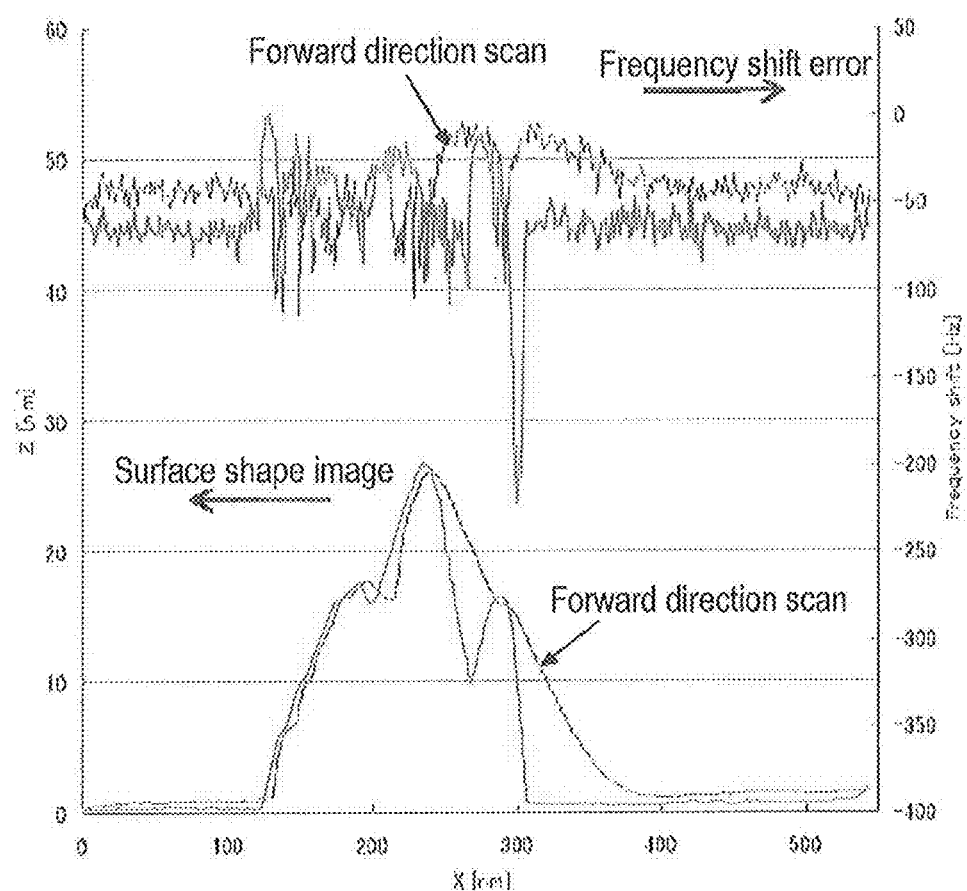
Figure 21:
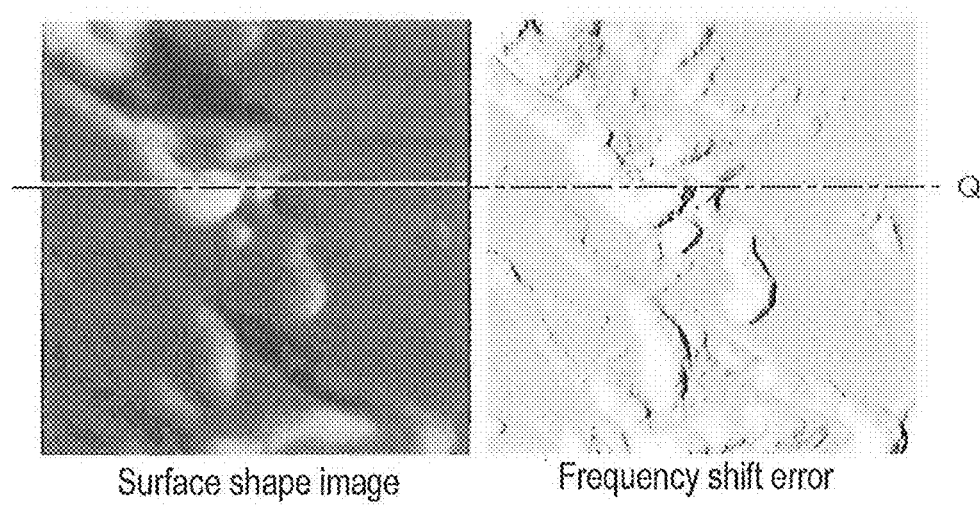
FIG. 21 is a graph showing frequency shift error with a reverse-direction scan using a conventional FM-AFM at the position of line Q.
Figure 21:
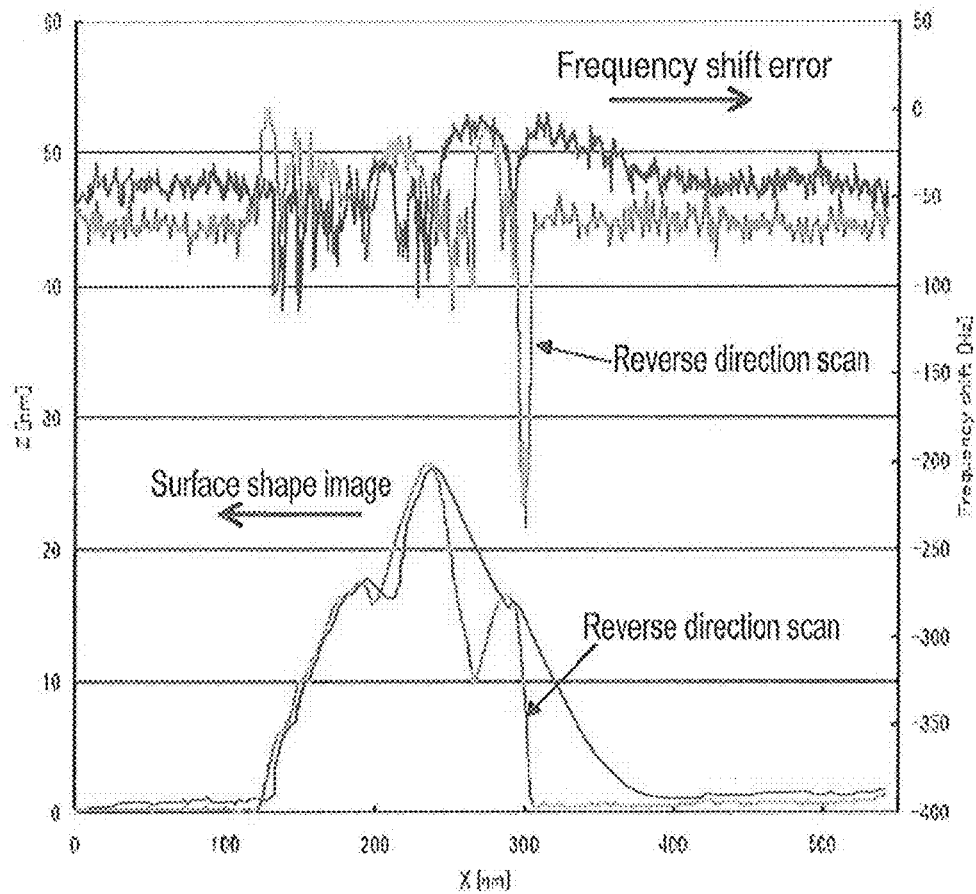

FIG. 20 and FIG. 21 are graphs that similarly show frequency shift errors at line Q between a forward-direction scan and a reverse-direction scan with a previous FM-AFM. Because these figures show a very large frequency shift error, it can be understood that feedback control had not fully stabilized.

Figure 22:
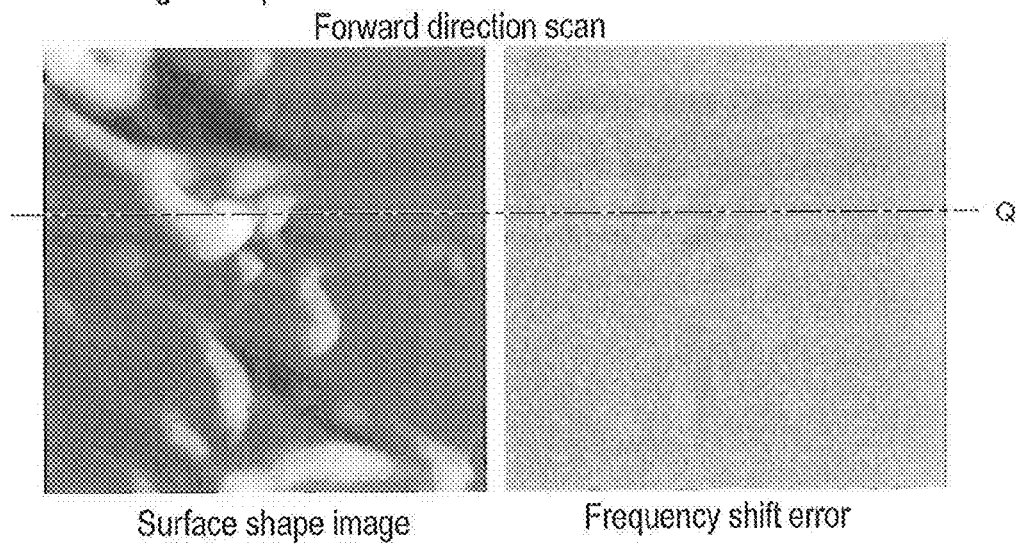
FIG. 22 is a graph showing frequency shift error and and sample height values obtained with the present embodiment as an FM-AFM using a forward-direction scan at the position of line Q.
Figure 22:
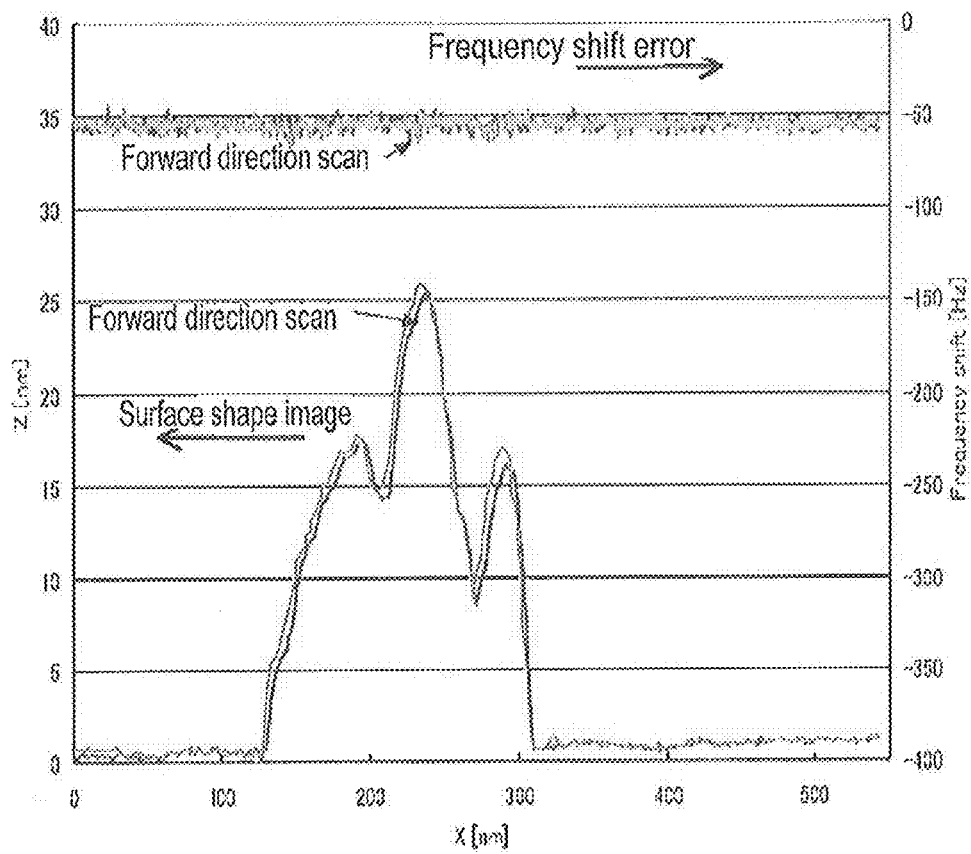
Figure 23:
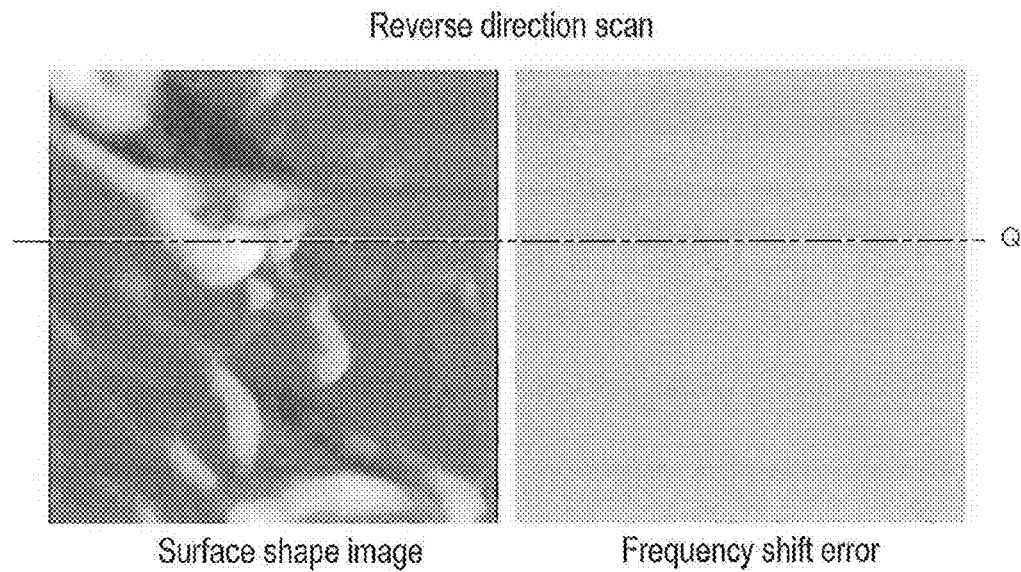
FIG. 23 is a graph showing frequency shift error and and sample height values obtained with the present embodiment as an FM-AFM using a reverse-direction scan at the position of line Q.
Figure 23:
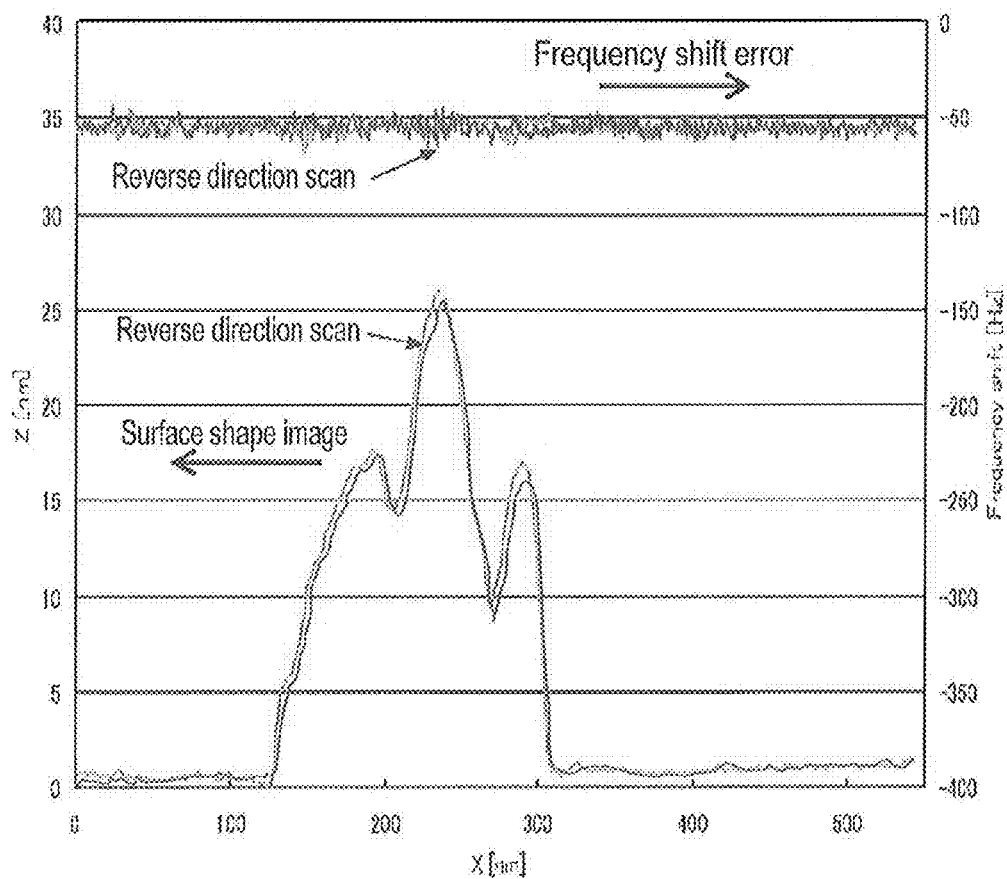

FIG. 22 and FIG. 23 are graphs that show actually measured values of sample height and frequency shift error at line Q for a forward-direction scan and a reverse-direction scan for a FM-AFM according to the present embodiment. The frequency shift error is confined to a very narrow range. It can be understood that feedback control is fully functioning, resulting in a good match between the measured heights of the sample in both the forward-direction scan and reverse-direction scan. This shows that concavities and convexities on the sample surface have been measured with a high accuracy.

Figure 24:
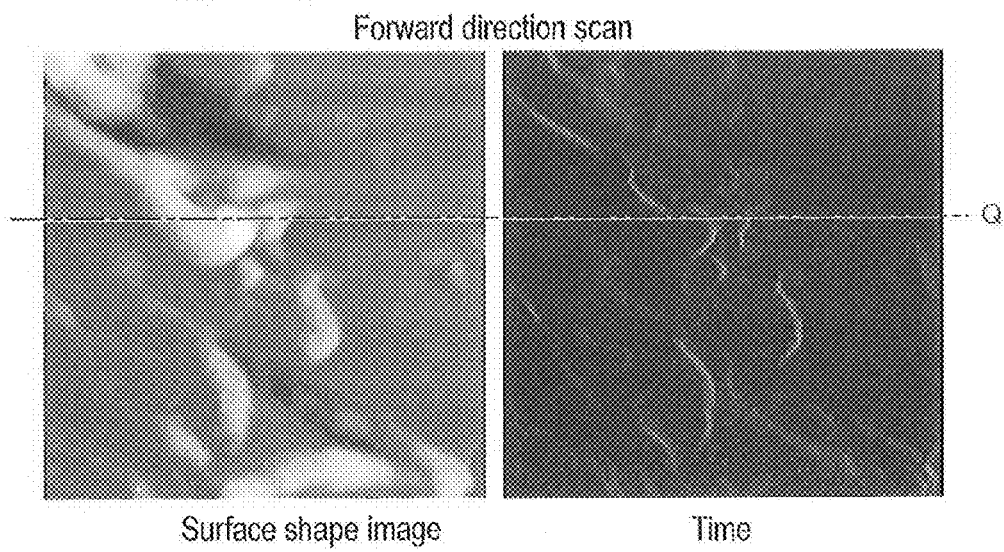
FIG. 24 is a graph showing measurement results and measurement time with a forward-direction scan at the position of line Q with the present embodiment as an FM-AFM.
Figure 24:
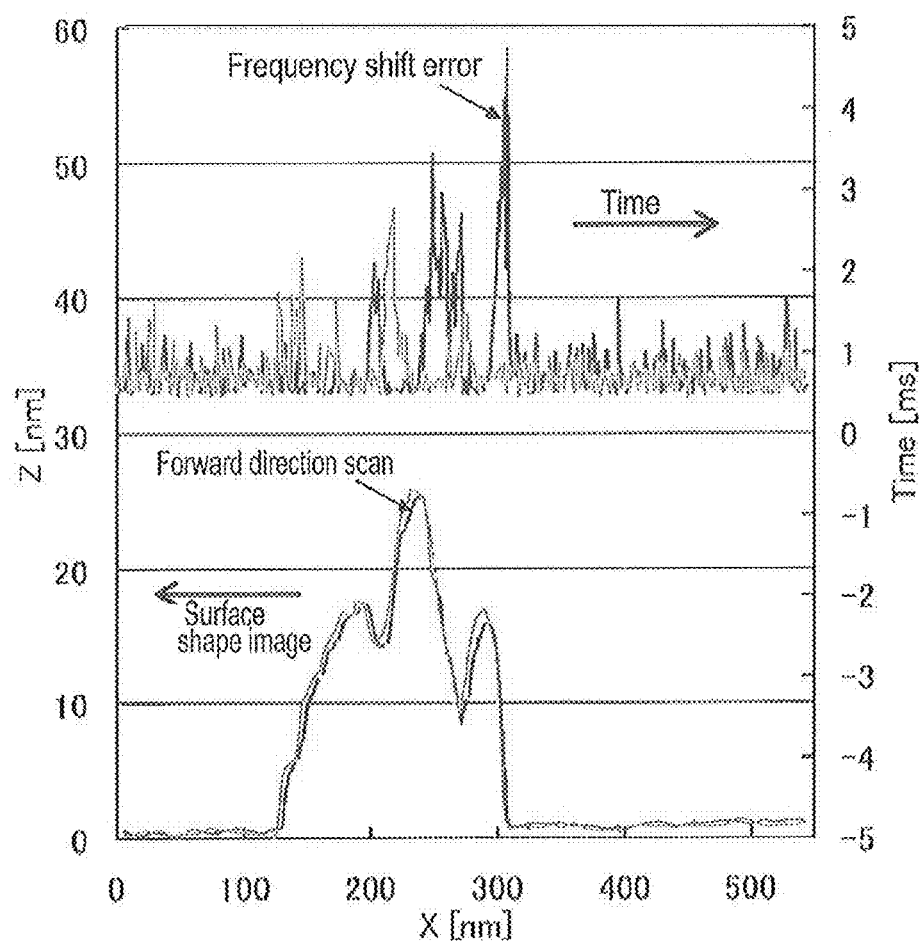
Figure 25:
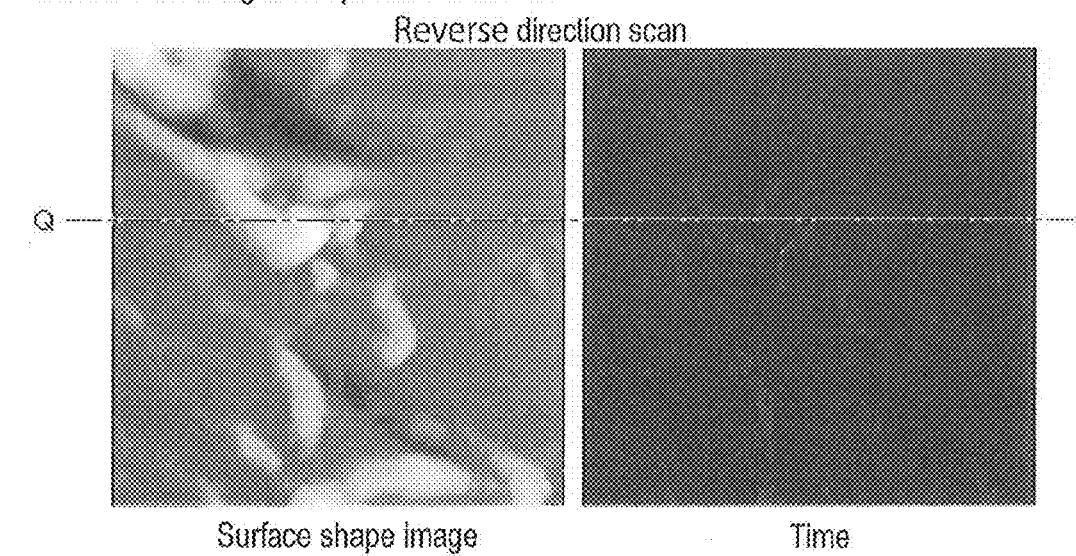
FIG. 25 is a graph showing measurement results and measurement time with a reverse-direction scan at the position of line Q with the present embodiment in an FM-AFM.
Figure 25:
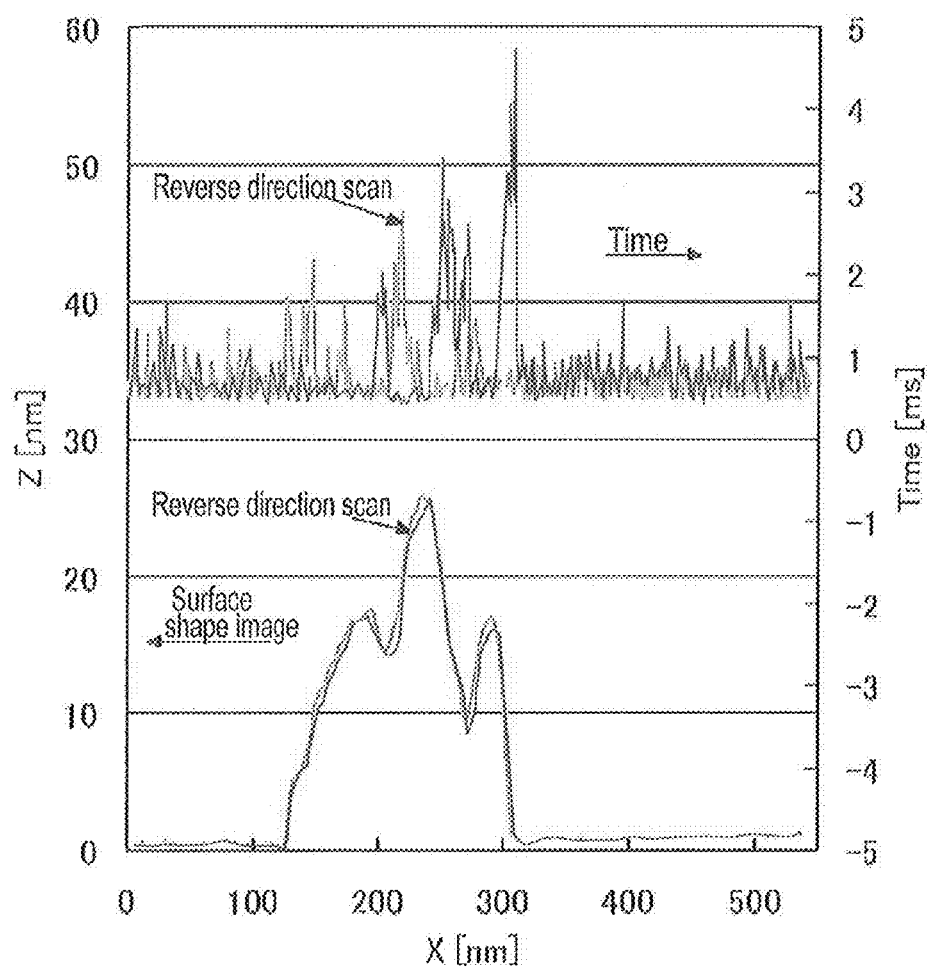

FIG. 24 and FIG. 25 are graphs that show the measurement time at the respective measurement points during a forward-direction scan and a reverse-direction scan with the present embodiment in a FM-AFM. It is evident that the measurement time is long where concavities and convexities are large on the sample surface and that the measurement time is short where the sample surface is flat.

Figure 26:
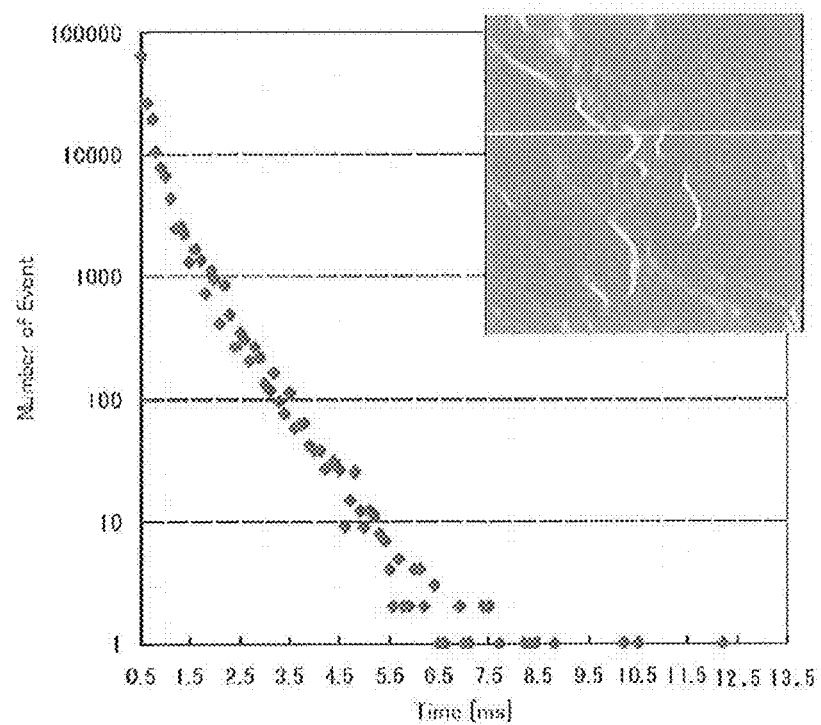
FIG. 26 is a graph showing the relationship between measurement time and the number of events at each measurement point with a forward-direction scan with the present embodiment in an FM-AFM.

FIG. 26 is a graph showing the relationship between measurement time and the frequency of its occurrence for a forward-direction scan of the respective measurement points. The longest measurement time that was actually observed, i.e., the longest time required for feedback control to stabilize, was 12.3 ms. If the scanning is performed using this maximum measurement time for each measurement point, 3936 seconds, or more than one hour, will be required for creating a single convex/concave image. Considering that, for practical use, a complete stabilization of feedback control is not required at each and every measurement point and that achieving a stabilization of feedback control at most measurement points is sufficient for practical use, the measurement time can be set to, for example, about 3.5 ms. When scanning is performed uniformly using this measurement time for each measurement point, a single convex/concave image can be created in 1120 seconds. This is still about 20 minutes. Furthermore, the measurements that are obtained at the measurement points where the feedback control cannot fully stabilize within a measurement time of 3.5 ms will not have a sufficiently high measurement accuracy.

In contrast with this, with the FM-AFM according to the present embodiment, it has been confirmed that the time required for creating a single convex/concave image is 261.3 seconds. In other words, as compared to even a previous FM-AFM where the measurement time at each measurement point was set to a value that was considered acceptable for practical use, the amount of time required for creating a single convex/concave image is only one-fourth, providing a large reduction in time. Furthermore, since it is guaranteed that the measurement results were obtained for all of the measurement points after a full stabilization of the feedback control, the measurement accuracy is also good.

The afore-described embodiments are just examples of the present invention, and needless to say, various modifications, changes and additions can be appropriately made within the claims of the present patent application and without deviating from the gist of the present invention.

What is claimed is:

1. A scan device for a microscope measurement instrument which performs a measurement by sequentially scanning each of a plurality of measurement points that are defined on a sample or a measurement instrument which performs a measurement by sequentially scanning each of a plurality of measurement points defined in terms of a physical measurement condition, said scanning device comprising:

a) n conditional decision means, where n is any integer equal to or greater than 2, for judging whether or not a condition defined in advance has been satisfied by each measurement point; and b) a scan control means which, if a decision is made by said n conditional decision means that all conditions have been satisfied by each measurement point, spatially moves the sample or the measurement system or changes the physical condition so as to move to the next measurement point.

2. The scan device according to claim 1 wherein, in moving from one measurement point to the next measurement point, at least two feedback controls are performed for spatially moving the sample or the measurement system or for changing the physical condition and said n conditional decision means judge whether or not an output of a feedback control loop for performing feedback control has become a constant or the variation in the output falls within an acceptable range.

3. The scan device according to claim 1 wherein, in moving from one measurement point to the next measurement point, at least two feedback controls are performed for spatially moving the sample or the measurement system or for changing the physical condition and said n conditional decision means judge whether or not the difference between a target value and an input value to a feedback control loop for performing feedback control is either zero or within an acceptable range.

4. The scan device according to claim 2 wherein, if said n conditional decision means judge whether or not the change in output or the difference in output falls within an acceptable range, a means is provided for a user to specify an acceptable range.

5. The scan device according to claim 2 wherein, if said n conditional decision means judge whether or not the change in output or the difference in output falls within an acceptable range, a range determination means is provided for automatically calculating an acceptable range based on output values from a feedback control loop at two or more different measurement points already scanned.

6. The scan device according to claim 1 wherein, if all conditions are not satisfied within a predetermined time at any measurement point, said scan control means forcibly changes a physical condition or spatially moves the sample or the measurement system so as to move to the next measurement point.

7. The scan device according to claims 1 wherein, if all conditions are not satisfied within a predetermined time at any measurement point, said scan control means suspends further scanning.

8. The scan device according to claim 2 that is used with a frequency modulation atomic force microscope which performs scanning while keeping a relative distance between a sample and a probe needle wherein said feedback control consists of two controls for controlling the separation distance between the probe needle and the sample and controlling the vibration amplitude of the probe needle.

9. The scan device according to claim 8 that is used with a Kelvin force microscope which performs scanning while keeping a relative distance between the sample and the probe needle wherein, in addition to the aforesaid two feedback controls, a feedback loop control is performed to compensate for a potential difference across the probe needle and the sample.

10. A scan device for use with a measurement instrument which performs a measurement by sequentially scanning each of a plurality of measurement points that are defined on a sample or a measurement instrument which performs a measurement by sequentially scanning each of a plurality of measurement points defined in terms of a physical measurement condition, said scanning device comprising:

n conditional decision means, where n is any integer equal to or greater than 2, for judging whether or not a condition defined in advance has been satisfied by each measurement point;

a scan control means which, if a decision is made by said n conditional decision means that all conditions have been satisfied by each measurement point, spatially moves the sample or the measurement system or changes the physical condition so as to move to the next measurement point; and a signal addition means that adds two or more types of signals that are acquired by measurement at each measurement point and said n conditional decision means judge whether or not the values of two or more types added by said signal addition means exceed a predetermined value defined in advance.

11. A scan device for use with a measurement instrument which performs measurements by sequentially scanning each of a plurality of measurement points that are defined on a sample or a measurement instrument which performs a measurement by sequentially scanning each of a plurality of measurement points defined in terms of a physical measurement condition, said scanning device comprising:

a) a signal addition means for adding signals acquired by measurement at each measurement point;

b) conditional decision means for judging whether or not an addition value obtained by said signal addition means exceeds a predetermined value; and c) a scan control means which, if said conditional decision means judge that the addition value has exceeded the predetermined value, spatially moves the sample or the measurement system or changes the physical condition so as to move to the next measurement point.

* * * * *